United States Patent
Ikeda et al.

(10) Patent No.: US 9,741,108 B2
(45) Date of Patent: Aug. 22, 2017

(54) IMAGE PROCESSING APPARATUS AND IMAGE PROCESSING SYSTEM FOR CONVEYOR TRACKING

(71) Applicant: OMRON Corporation, Kyoto-shi (JP)

(72) Inventors: Yasuyuki Ikeda, Kyoto (JP); Yuichi Doi, Kusatsu (JP); Naoya Nakashita, Kyoto (JP)

(73) Assignee: OMRON Corporation, Kyoto-shi (JP)

( * ) Notice: Subject to any disclaimer, the term of this patent is extended or adjusted under 35 U.S.C. 154(b) by 456 days.

(21) Appl. No.: 13/957,467

(22) Filed: Aug. 2, 2013

(65) Prior Publication Data

US 2013/0329954 A1 Dec. 12, 2013

Related U.S. Application Data

(63) Continuation of application No. PCT/JP2011/056230, filed on Mar. 16, 2011.

(30) Foreign Application Priority Data

Feb. 15, 2011 (JP) .................................. 2011-029435

(51) Int. Cl.
  *G06K 9/00* (2006.01)
  *G06T 7/00* (2017.01)
  (Continued)

(52) U.S. Cl.
  CPC ........ *G06T 7/0004* (2013.01); *B23Q 17/2414* (2013.01); *G06T 1/0007* (2013.01);
  (Continued)

(58) Field of Classification Search
  CPC .......... G01N 2021/845; G06K 2209/19; G06T 7/0004; G06T 2207/30164; G06T 1/0014;
  (Continued)

(56) References Cited

U.S. PATENT DOCUMENTS 4,613,269 A * 9/1986 Wilder et al. ................. 700/259
4,876,728 A * 10/1989 Roth ............................. 382/153
(Continued)

FOREIGN PATENT DOCUMENTS

JP H09-072717 A 3/1997
JP H10-139146 A 5/1998
(Continued)

OTHER PUBLICATIONS

"Vision Sensor Conveyor Synchronization Function" TS3000series Robot Controller Instruction Manual. Numazu: Toshiba Machine, 2010. pp. 1-21. Print.*
(Continued)

*Primary Examiner* — Eric Rush
(74) *Attorney, Agent, or Firm* — Mots Law, PLLC

(57) ABSTRACT

An image processing apparatus, connected to an imaging part to capture an image of workpieces conveyed on a conveyer, includes an interface that receives a signal indicating a travel distance of the conveyer, an interface that communicates with a control device for controlling a moving machine disposed downstream of an imaging area of a imaging part, a positional information acquisition unit that processes the image captured by the imaging part and thereby acquiring positional information of a pre-registered workpiece in the image, a travel distance obtaining unit that obtains the travel distance of the conveyer synchronized with the control device, an initiating unit that initiates the capturing by the imaging part in response to an imaging command, and a transmission unit that transmits, to the control device, the positional information and the travel distance upon the capturing of the image used to acquire the positional information.

17 Claims, 17 Drawing Sheets

(51) Int. Cl.
*B23Q 17/24* (2006.01)
*G06T 1/00* (2006.01)
*G01N 21/84* (2006.01)

(52) U.S. Cl.
CPC ...... *G06T 1/0014* (2013.01); *G01N 2021/845* (2013.01); *G05B 2219/31432* (2013.01); *G06K 2209/19* (2013.01); *G06T 2207/30108* (2013.01)

(58) Field of Classification Search
CPC ............ B23Q 2707/16; B23Q 17/2414; B23Q 17/2428; B23Q 17/249; G05B 2219/31432; G05B 2219/37555
USPC .... 382/141, 103, 152, 100, 153; 348/91, 94, 348/95; 700/112, 213, 228–230, 245, 700/251, 259
See application file for complete search history.

(56) References Cited

U.S. PATENT DOCUMENTS

| | | | |
|---|---|---|---|
| 5,041,907 A * | 8/1991 | Sager | B07C 5/3422 348/91 |
| 6,360,142 B1 | 3/2002 | Miura et al. | |
| 6,483,935 B1 * | 11/2002 | Rostami | G01N 21/8901 382/141 |
| 7,259,854 B2 * | 8/2007 | Schnell | B65G 43/02 198/502.1 |
| 7,654,380 B2 | 2/2010 | Nishihara et al. | |
| 7,760,391 B2 | 7/2010 | Kitamura et al. | |
| 2005/0075752 A1 * | 4/2005 | Ban | B25J 9/1697 700/213 |
| 2007/0007924 A1 * | 1/2007 | Nishihara | B25J 9/0093 318/560 |
| 2007/0073439 A1 * | 3/2007 | Habibi et al. | 700/213 |
| 2008/0301072 A1 | 12/2008 | Nagatsuka et al. | |
| 2009/0323094 A1 * | 12/2009 | Hayashi et al. | 358/1.12 |
| 2010/0063625 A1 * | 3/2010 | Krause | G05B 19/4182 700/245 |
| 2010/0094453 A1 | 4/2010 | Nishihara et al. | |
| 2010/0226561 A1 * | 9/2010 | Fujikawa et al. | 382/141 |
| 2011/0175997 A1 * | 7/2011 | Case | G01N 21/8903 348/92 |

FOREIGN PATENT DOCUMENTS

| | | |
|---|---|---|
| JP | H10-249766 A | 9/1998 |
| JP | 2000-071188 A | 3/2000 |
| JP | 2002-37441 A | 2/2002 |
| JP | 2005-063176 A | 3/2005 |
| JP | 2005-111607 A | 4/2005 |
| JP | 2005-262369 A | 9/2005 |
| JP | 2005-293567 A | 10/2005 |
| JP | 2007-15055 A | 1/2007 |
| JP | 2007-033328 A | 2/2007 |
| JP | 2008-296330 A | 12/2008 |
| JP | 2009-297881 A | 12/2009 |
| WO | 2006075354 A1 | 7/2006 |

OTHER PUBLICATIONS

Encoder Information—Application Notes. 1.1st ed. Ettlingen, Germany: Vision Components GmbH, 2007. Print.*
The Extended European search report issued on Jun. 18, 2015 in the counterpart European application.

* cited by examiner

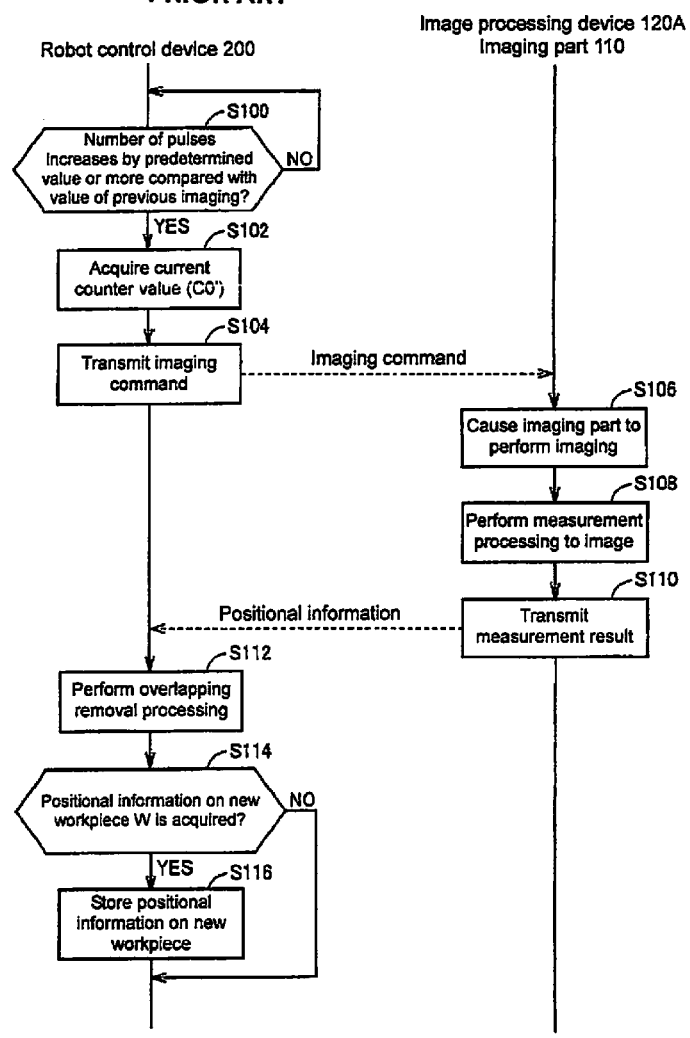

Fig. 8

| 3 | X1 | Y1 | θ1 | X2 | Y2 | θ2 | X3 | Y3 | θ3 | 100 |

Number of detected workpieces — Workpiece 1, Workpiece 2, Workpiece 3 (Coordinate value) — Counter value

US 9,741,108 B2

IMAGE PROCESSING APPARATUS AND IMAGE PROCESSING SYSTEM FOR CONVEYOR TRACKING

CROSS REFERENCE TO RELATED APPLICATIONS

This application is a Continuation of PCT Application No. PCT/JP2011/056230 filed on Mar. 16, 2011, and claims the priority of Japanese Patent Application No. 2011-029435 filed on Feb. 15, 2011, entitled "IMAGE PROCESSING APPARATUS AND IMAGE PROCESSING SYSTEM," the entire contents of both of which are incorporated herein by reference.

TECHNICAL FIELD

This disclosure relates to an image processing apparatus and an image processing system that are directed to conveyer tracking or the like.

BACKGROUND ART

In a factory automation (FA) field, a technique for controlling various processes using image processing is frequently used for the purpose of labor-saving. As an application example of such an image processing technique, there has been know a process in which while a conveyer such as a belt conveyer conveys workpieces, a moving machine (hereinafter referred to as an "industrial robot" or simply referred to as a "robot") tracks and grasps the conveyed workpieces. The work process is called conveyer tracking or the like.

In the conveyer tracking technique, an imaging device images the workpiece on the conveyer, and an image processing apparatus performs measurement processing such as pattern matching and binarization processing to an image obtained by the imaging device, thereby identifying an existence position (a coordinate) of each workpiece. The robot tracks and grasps each workpiece based on the identified position (the coordinate) of each workpiece.

For example, Patent Document 1 (Japanese Unexamined Patent Publication No. 09-072717) discloses a configuration that is applied to tracking processing or the like of the robot by performing image acquisition/image processing with a simple system in which a visual sensor is used.

Although not used in the conveyer tracking, for example, Patent Document 2 (Japanese Unexamined Patent Publication No. 2005-293567), Patent Document 3 (Japanese Unexamined Patent Publication No. 2005-063176), and Patent Document 4 (International Patent Publication WO2006/075354) can be cited as prior art documents related to the visual sensor.

Patent Document 2 discloses a measurement device that can output a measured value of a measurement target to an external control device together with information on the time when the measured value is obtained.

Patent Document 3 discloses an object recognition device that recognizes a state of the workpiece by performing the image processing to an imaging result of an object, such as the workpiece on the conveyer, which moves relative to imaging part. Particularly, Patent Document 3 discloses the object recognition device that can accurately obtain a positional relationship between the imaging part and the workpiece at imaging timing and an image processing result.

Patent Document 4 discloses a configuration in which, although not used in the conveyer tracking, in the case where the workpiece as a semiconductor chip is placed on an XY-table without performing positioning, the workpiece is imaged with a camera to position the workpiece to a previously assigned position.

SUMMARY OF THE INVENTION

In the configuration of Patent Document 1, a pulse coder is attached to the conveyer in order to detect a travel distance, and detection output from the pulse coder is input to a robot control part. The visual sensor including the image processing apparatus and the camera performs the imaging and the tracking using the detection output of the pulse coder.

In the configuration of Patent Document 1, an imaging command is issued to the visual sensor at the timing at which the image processing apparatus determines that the detection output from the pulse coder satisfies a predetermined condition. However, the timing at which the imaging command is issued to the visual sensor does not completely agree with the timing at which the visual sensor actually performs the imaging, and a time lag is generated to some extent. Although the time lag does not cause trouble in the case where a conveying speed of the conveyer is slow relative to a length of the time lag, the time lag causes a deviation of the tracking when the conveying speed of the conveyer is relatively fast.

Therefore, Patent Document 2 discloses one of approaches to solve the time lag. More specifically, Patent Document 2 discloses the configuration, in which a measurement control part is provided in a signal processing part to measure the time for the measurement and a measurement result is output while temporal information on the measurement is added to the measurement result. When the configuration of Patent Document 2 is applied to the conveyer tracking, an influence of the time lag can be reduced by calculating a travel distance based on the temporal information on the measurement in the case where the conveying speed of the conveyer is kept constant.

However, because the conveying speed of the conveyer changes in an actual production line, the tracking processing may not be reliably performed only by directly applying the technique of Patent Document 2.

Patent Document 3 discloses the configuration in which the imaging timing is generated using not the measurement result of an encoder but a trigger sensor provided independently of the encoder. In this configuration, because the time lag between the timing at which an arrival of the workpiece is detected and the timing at which the imaging is performed is generated by the trigger sensor, information on a positional relationship between the workpiece in the imaging and the imaging part is generated using the measurement result of the encoder, and the image is recognized using the information on the positional relationship.

However, in the actual production line, a plurality of workpieces are frequently disposed on a conveying route. Therefore, it is not realistic that the trigger sensor disclosed in Patent Document 3 detects the arrival of the workpiece. For this reason, the tracking processing cannot be reliably performed even if the technique of Patent Document 3 is adopted.

In Patent Document 4, a position detection signal is transmitted from a position detector to the image processing apparatus through a motor control device. In the image processing apparatus, while the camera images the semiconductor chip, the motor control device is controlled based on a position command signal from a master device and the position detection signal from the position detector. In the configuration disclosed in Patent Document 4, it is assumed that a transmission delay of the position detection signal that is transmitted from the position detector to the image processing apparatus through the motor control device is relatively negligible compared with a positioning control cycle of the XY-table. Therefore, the technique of Patent Document 4 cannot directly be applied to the conveyer tracking or the like. For this reason, the tracking processing cannot be reliably performed even if the technique of Patent Document 4 is adopted.

An object of an embodiment of the invention is to provide a visual sensor that can accurately perform the tracking processing even if the time lag exists until the imaging is actually performed after the imaging command is issued to the imaging device.

An aspect of the invention provides an image processing apparatus which is connected to an imaging part, the imaging part being disposed to capture an image of a workpiece conveyed on a conveyer. The image processing apparatus includes: an interface that receives a signal indicating a travel distance of the conveyer in a conveying route; an interface that communicates with a control device for controlling a moving machine for handling the workpiece, the moving machine being disposed downstream of an imaging area of the imaging part in the conveying route; a positional information acquisition unit that processes the image captured by the imaging part and thereby acquiring positional information on a region corresponding to a pre-registered workpiece in the image; a travel distance obtaining unit that obtains the travel distance of the conveyer synchronized with the control device; an initiating unit that initiates the capturing of the image by the imaging part in response to an imaging command; and a transmission unit that transmits, to the control device, the positional information and the travel distance when capturing of the image used to acquire the positional information.

The positional information may include a coordinate value in which the region corresponding to the pre-registered workpiece in the image is expressed in a coordinate system of the moving machine.

The positional information may further include a rotation angle of the region corresponding to the workpiece in the image, the rotation angle being based on an attitude of the pre-registered workpiece.

The signal indicating the travel distance of the conveyer in the conveying route may be a pulse signal.

The pulse signal may be input to the image processing apparatus and the control device. The travel distance obtaining unit may include a first counter that counts the number of pulses included in the pulse signal. An identical parameter may be set with respect to counting between the first counter and a second counter, the second counter used by the control device to count the number of pulses included in the pulse signal.

The first counter and the second counter may be reset before the counting of the number of pulses included in the pulse signal is started.

Alternatively, the pulse signal may be input to the image processing apparatus, the travel distance obtaining unit may include a counter that counts the number of pulses included in the pulse signal, and the transmission unit may be configured such that a delay time related to transmission and reception is kept constant.

The travel distance when capturing of the image used to acquire the positional information may be indicated by a counter value of the counter.

The image processing apparatus may be configured to receive the imaging command from the control device.

Another aspect of the invention provides an image processing system including: an imaging part disposed to capture an image of a workpiece conveyed on a conveyer; a control device that controls a moving machine for handling the workpiece, the moving machine being disposed downstream of an imaging area of the imaging part in a conveying route; and an image processing apparatus that is connected to the imaging part and the control device. The image processing apparatus includes: an interface that receives a signal indicating a travel distance of the conveyer in the conveying route; a positional information acquisition unit that that processes the image captured the imaging part and thereby acquiring positional information on a region corresponding to a pre-registered workpiece in the image; a travel distance obtaining unit that obtains the travel distance of the conveyer synchronized with the control device; an initiating unit that initiates the capturing of the image by the imaging part in response to an imaging command; and a transmission unit that transmits, to the control device, the positional information and the travel distance when capturing of the image used to acquire the positional information.

According to the above aspects, even if the time lag exists until the imaging is actually performed after the imaging command is issued to the imaging device, the image processing apparatus and the image processing system including the image processing apparatus can accurately perform the tracking processing.

BRIEF DESCRIPTION OF THE DRAWINGS

FIG. 5 is a sequence diagram illustrating a control operation in a tracking system according to the related art.

FIG. 8 is a view illustrating a format example of a measurement result transmitted in the tracking system according to the first embodiment of the invention.

DETAILED DESCRIPTION

Figure 1:
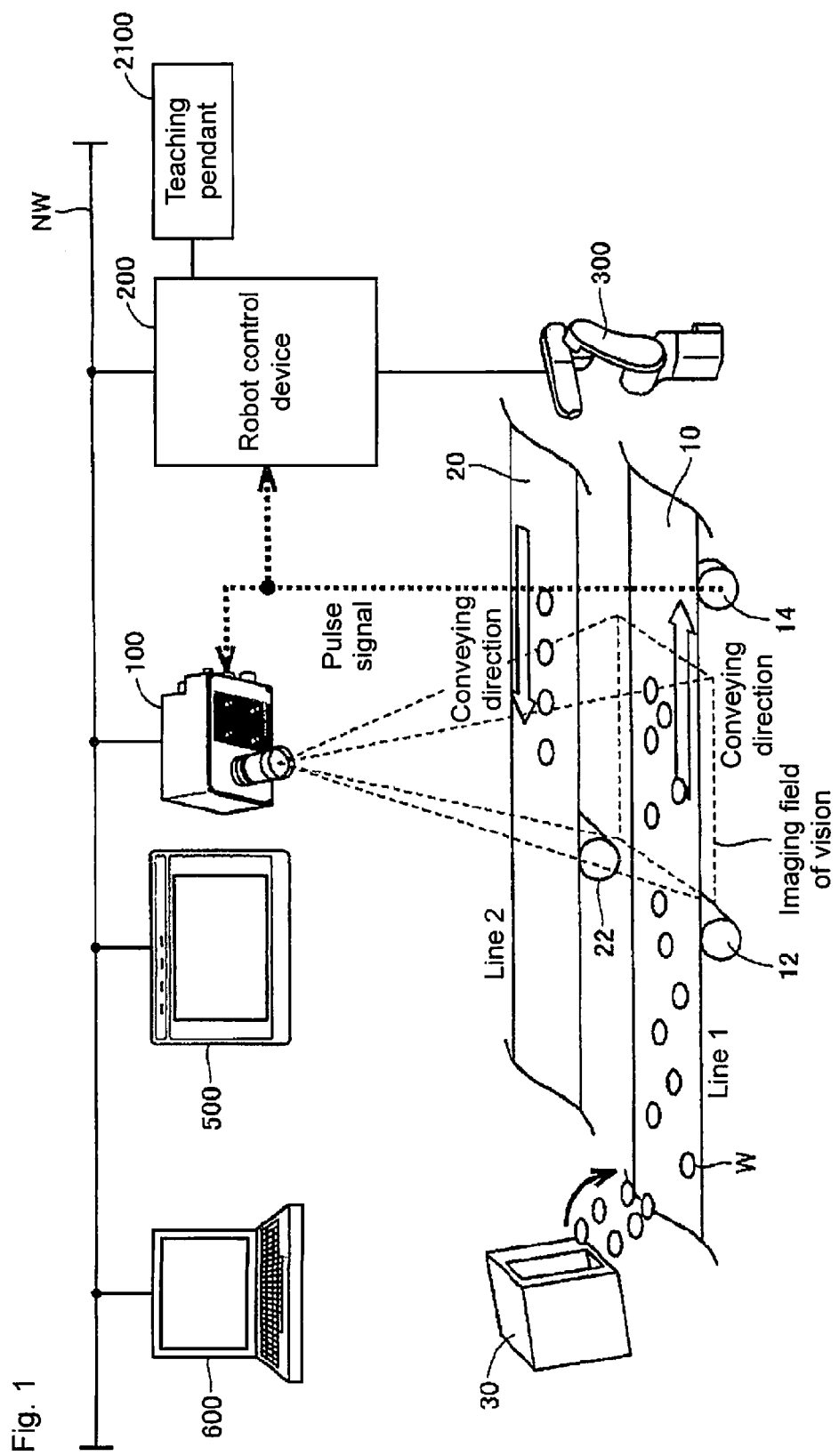
FIG. 1 is a schematic diagram illustrating a configuration of a conveyer tracking system using a visual sensor according to a first embodiment of the invention.

Embodiments of the invention will be described in detail with reference to the drawings. The same or equivalent component is designated by the same reference numeral in the drawings, and its description is not repeated for sake of brevity.

First Embodiment

A. System Configuration

FIG. 1 is a schematic diagram illustrating a configuration of a conveyer tracking system using a visual sensor according to a first embodiment of the invention. The conveyer tracking system in FIG. 1 includes two conveyers 10 and 20. The conveyers 10 and 20 are rotated and driven by driving rollers 12 and 22, respectively. Hereinafter, the conveyer 10 and 20 are also referred to as a line 1 and a line 2, respectively. In the example in FIG. 1, the line 1 moves rightward and the line 2 moves leftward in the plane of the drawing. Workpieces W are randomly provided to the line 1 from the left side by a discharging device 30 or the like. The workpieces W on the line 1 travel from the left side toward the right side. Typically, foods such as a snack or various tablets are conceivable as the workpiece W.

A visual sensor 100 of the first embodiment is provided at a predetermined position above the line 1. As described later, an imaging part that images such subjects as the workpieces and an image processing part that processes an image imaged by the imaging part are integrally formed in the visual sensor 100. Alternatively, the imaging part and the image processing part may be separately formed.

The visual sensor 100 is placed such that an imaging field of vision (or an imaging area) of the visual sensor 100 covers the whole of the line 1 in a width direction (a direction orthogonal to a conveying direction). The visual sensor 100 performs imaging at a predetermined cycle, which allows the workpieces W flowing randomly on the line 1 to be sequentially imaged. The visual sensor 100 performs measurement processing such as pattern matching to the sequentially-imaged image, for positioning processing and tracking processing to each workpiece. The imaging part (an imaging part 110 in FIG. 3) of the visual sensor 100 is disposed so as to image the workpiece W conveyed on the conveyer 10.

An image processing apparatus (an image processing part 120 in FIG. 3) is connected to the imaging part.

A robot 300, which can grasp the workpiece W on the line 1 and move the workpiece W to the line 2, is disposed downstream of the visual sensor 100 in the conveying direction of the line 1. The robot 300 includes an arm that grasps the workpiece W, and thus the robot 300 can move the arm to a target position to grasp the workpiece on the line 1. That is, the robot 300 functions as a moving machine, which is disposed downstream of the imaging area of the imaging part of the visual sensor 100 in the conveying route of the conveyer 10 (the line 1), and handles the workpiece W. More specifically, the robot 300 positions the arm at the target workpiece W on the line 1, picks up the workpiece W, and arranges the workpiece W on the line 2.

The robot 300 is disposed on a movement mechanism 400 (see FIG. 2) which travels along the line 1, so that the robot 300 can move in a predetermined travel range. The travel range of the robot 300 is also referred to as a tracking range.

The tracking processing and the positioning processing of the robot 300 are controlled using a detection result of an encoder 14 provided in the line 1. Typically, a rotary encoder is used as the encoder 14, and the encoder 14 generates a pulse signal in association with its rotation. When the number of pulses of the generated pulse signal, the number of rotations of the roller coupled to the conveyer 10 (the line 1), namely, the pulse signal generated by the encoder 14 corresponds to a signal indicating the travel distance of the conveyer 10 in the conveying route, and the travel distance of the conveyer 10 is calculated based on the pulse signal.

The robot 300 operates in response to a command from a robot control device 200. That is, the robot control device 200 is a control device for controlling the robot 300 (that is, the moving machine). The robot control device 200 is connected to the visual sensor 100 through a network NW, and issues the command necessary for the action to grasp each workpiece W to the robot 300 based on the position of the workpiece W detected by the visual sensor 100.

A teaching pendant 2100 is connected to the robot control device 200 in order to calibrate the robot 300. A user operates the teaching pendant 2100 to move the robot 300 to the position necessary for the calibration.

In addition to the visual sensor 100 and the robot control device 200, an operation display device 500 and a support device 600 may be connected to the network NW. The operation display device 500 displays a processing result from the visual sensor 100 and an operating state of the robot 300 from the robot control device 200, and issues various commands to the visual sensor 100 and/or the robot control device 200 in response to an input from the user.

In the conveyer tracking system in FIG. 1, there is a potential need to enhance a line speed (a conveying speed) in order to improve productivity. In order to meet the need, the conveyer tracking system of the this embodiment has the configuration in which the pulse signal generated by the encoder 14 is input to not only the robot control device 200 but also to the visual sensor 100. Even if the delay time becomes problematic in the communication between the robot control device 200 and the visual sensor 100 through the network NW, an influence of the delay time can be avoided by acquiring the positional information on the target conveyer in synchronization with the visual sensor 100 and the robot control device 200. The details are described later.

B. Positioning Processing and Tracking Processing

The positioning processing and the tracking processing in the conveyer system in FIG. 1 will be described below in detail.

Figure 2:
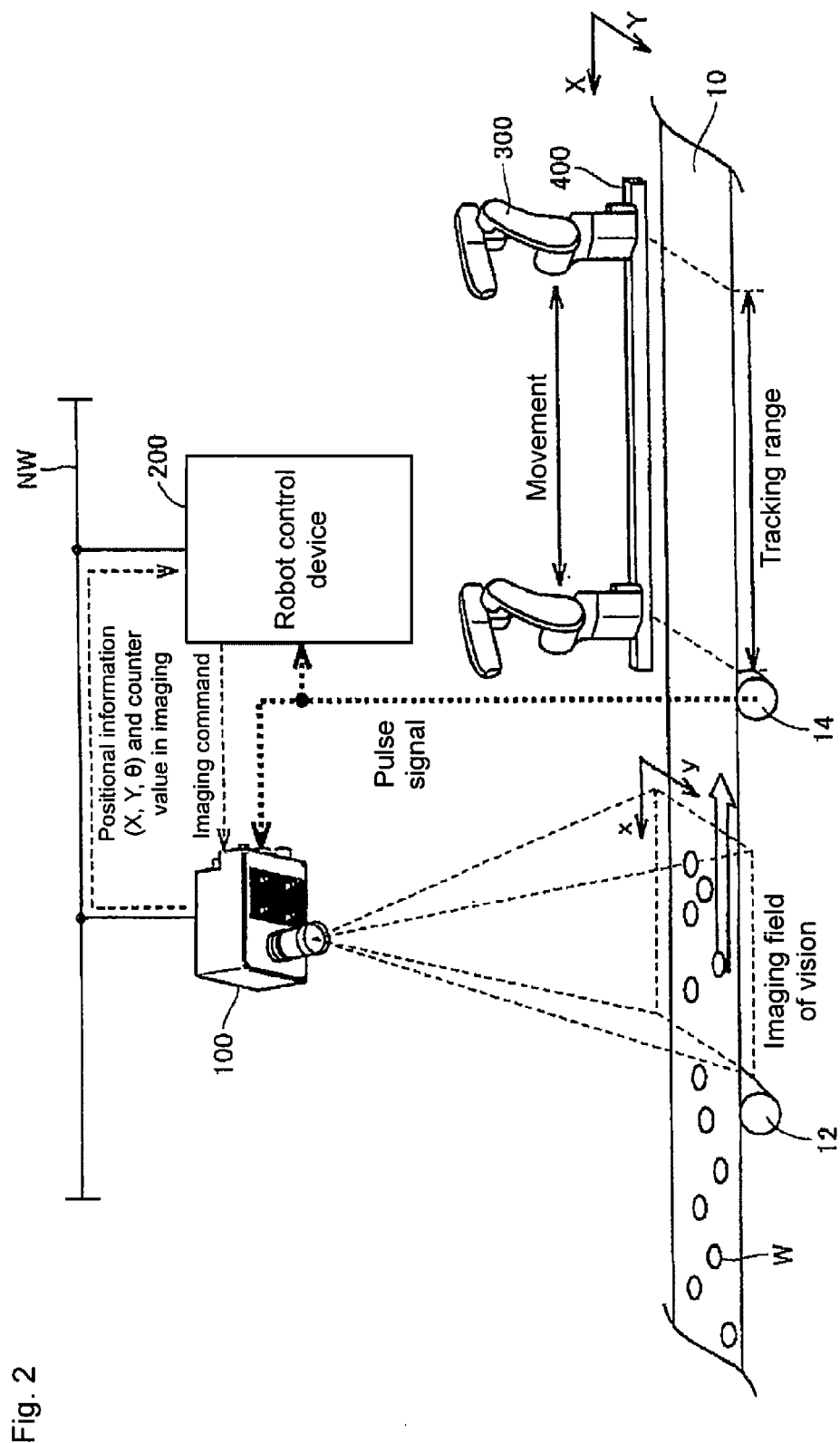
FIG. 2 is a view illustrating positioning processing and tracking processing in the conveyer tracking system using the visual sensor according to the first embodiment of the invention.

FIG. 2 is a view illustrating the positioning processing and the tracking processing in the conveyer tracking system with the visual sensor according to the first embodiment of the invention. Referring to FIG. 2, the visual sensor 100 images the line 1 using the built-in imaging part. The imaging by the visual sensor 100 is initiated in response to an imaging command from the robot control device 200. The imaging command is transmitted through the network NW that connects the visual sensor 100 and the robot control device 200. Typically, general-purpose networks such as Ethernet (registered trademark) can be used as the network NW.

The visual sensor 100 is configured to receive the imaging command from the robot control device 200, and initiates the imaging in response to the imaging command. Therefore, the visual sensor 100 sequentially acquires the image in which the imaging field of vision is taken. The visual sensor 100 performs measurement processing, i.e., pattern matching processing based on a model image of the pre-registered workpiece W, or binarization processing, to the image. The visual sensor 100 then transmits, to the robot control device 200, positional information (X, Y, θ) of each workpiece W when being captured, which is obtained by the measurement processing. Thus, the visual sensor 100 performs the measurement processing on the image captured by the imaging part, thereby acquiring the positional information on the region corresponding to the pre-registered workpiece in the image.

The positional information includes a position (X, Y) of the workpiece W on the conveyer 10 and a rotation angle (θ) of the workpiece W. From the viewpoint of simplifying overlapping removal processing in the robot control device 200, a value converted into a coordinate system controlling the robot 300 is used as the position (X, Y) of the workpiece W. For example, as illustrated in FIG. 2, the arm (picking) position of the robot 300 is defined in an X-coordinate (the conveying direction of the conveyer) and a Y-coordinate (the direction orthogonal to the conveying direction of the conveyer). The position of each workpiece detected by the pattern matching processing is identified using the XY-coordinate system (hereinafter also referred to as a "robot coordinate system"). That is, the positional information includes a coordinate value in which the region corresponding to the pre-registered workpiece in the image acquired by the imaging is expressed in the coordinate system "robot coordinate system" of the robot 300 (the moving machine). The visual sensor 100 and the robot control device 200 are previously calibrated so as to be able to output the measured positional information on each workpiece W as the value of the robot coordinate system.

The rotation angle (θ) of the workpiece W means a rotation angle with respect to the model image of the workpiece W. That is, the positional information further includes the rotation angle of the region corresponding to the workpiece in the image, and the rotation angle is based on an attitude of the pre-registered workpiece. Depending on a shape of the workpiece W, the rotation angle of the arm of the robot 300 and the like are properly controlled based on the information on the rotation angle.

More specifically, the robot control device 200 counts the number of pulses in the pulse signal from the encoder 14, and the robot control device 200 transmits the imaging command to the visual sensor 100 through the network NW at the time the counted number of pulses becomes greater than or equal to a predetermined value.

The positional information on each workpiece from the visual sensor 100 is transmitted to the robot control device 200 through the network NW, and stored in a memory of the robot control device 200. Because the visual sensor 100 sequentially performs the imaging, sometimes the identical workpiece W is imaged at different timings. In such cases, the overlapping pieces of positional information on the identical workpiece W are transmitted to the robot control device 200. However, in the robot control device 200, the positional information is stored in the memory after the overlapping pieces of positional information are removed. Every time the pulse signal is received from the encoder 14, the robot control device 200 updates all the pieces of positional information (the coordinate values (X, Y)) on the workpieces W stored in the memory. This is because the workpiece W actually conveyed on the belt conveyer is tracked on the memory of the robot control device 200. When the updated positional information (the coordinate value) on any one of the workpieces W enters a tracking range of the robot 300, the robot control device 200 issues the command necessary for the grasping action to the robot 300.

The pulse signal, which is generated according to a detection result of the encoder 14 provided in the line 1, is configured to be input to the visual sensor 100 and the robot control device 200. Each of the visual sensor 100 and the robot control device 200 includes an encoder counter that counts the number of pulses included in the pulse signal. The pulse signal is concurrently input from the encoder 14 to the visual sensor 100 and the robot control device 200. Therefore when the encoder counters of the visual sensor 100 and the robot control device 200 are initialized (the counters are reset) at the identical timing, the counter values become identical with respect to the subsequently-input pulse signal, namely, the counter values can be synchronized with each other.

More specifically, a travel distance of the conveyer per pulse included in the pulse signal from the encoder 14 is previously set in the visual sensor 100 and the robot control device 200. Additionally, identical parameters such as a counter maximum value, a counter minimum value, and an increasing value per pulse are set to the encoder counters of the visual sensor 100 and the robot control device 200. That is, the identical parameters are set with respect to the counting between the encoder counter of the visual sensor 100 and the encoder counter of the robot control device 200.

The counter values of the encoder counters are initialized to zero before the production line operates. That is, the encoder counters of the visual sensor 100 and the robot control device 200 are reset before the counting of the number of pulses included in the pulse signal is started.

In this embodiment, the travel distance of the conveyer 10 in the conveying route between the visual sensor 100 and the robot control device 200 synchronously maintained.

Particularly, the visual sensor 100 of the this embodiment transmits to the robot control device 200 the counter value in actually performing the imaging in response to the imaging command from the robot control device 200 while adding the counter value to the positional information on each workpiece. As described above, because the visual sensor 100 and the robot control device 200 maintain the counter value in synchronization with each other, even if the time lag exists between the timing at which the imaging command is transmitted from the robot control device 200 and the timing at which the visual sensor 100 actually performs the imaging in response to the imaging command, the timing at which the imaging is actually performed is identified on a common temporal axis, namely, using the synchronized counter value.

Thus, the visual sensor 100 transmits, to the robot control device 200, the positional information on the detected workpiece W and the travel distance of the conveyer 10 during the capturing of the image used to acquire the positional information. The travel distance in imaging the image used to acquire the positional information on the workpiece W is indicated by the counter value of the counter.

In the robot control device 200, the corresponding positional information is corrected using the counter value in the imaging, the counter value being received from the visual sensor 100, and the corrected positional information is stored in the memory. Therefore, a situation can be avoided where the time lag until the actual imaging after the output of the imaging command due to the high line speed has an influence on the positioning processing and the tracking processing in the robot 300.

C. Hardware Configuration

Figure 3:
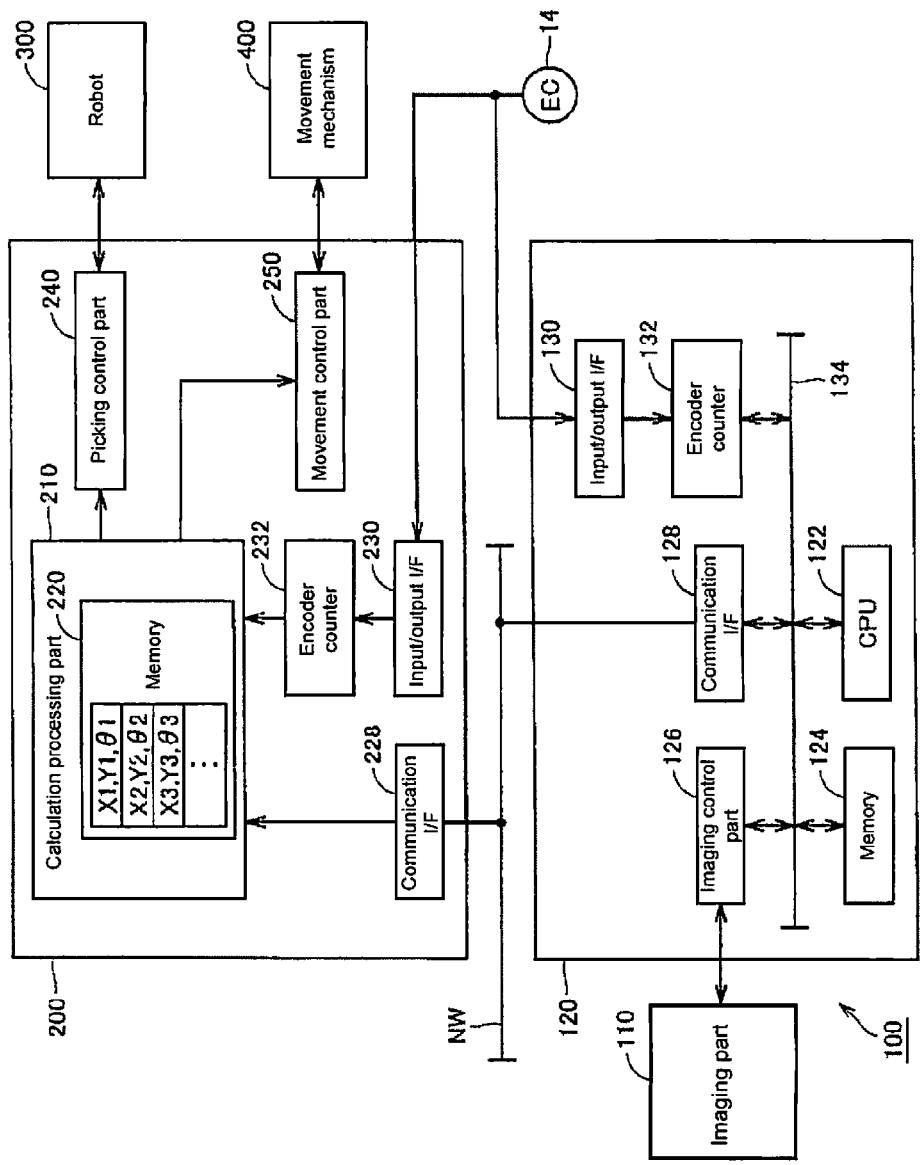
FIG. 3 is a schematic diagram illustrating a hardware configuration of the conveyer tracking system using the visual sensor according to the first embodiment of the invention.

FIG. 3 is a schematic diagram illustrating a hardware configuration of the conveyer tracking system using the visual sensor according to the first embodiment of the invention. Referring to FIG. 3, the visual sensor 100 includes an imaging part 110 and an image processing part 120.

The imaging part 110 is a device that images the subject existing in the imaging field of vision. The imaging part 110 includes an optical system such as a lens and a diaphragm, and a light receiving element such as a CCD (Charge Coupled Device) image sensor and a CMOS (Complementary Metal Oxide Semiconductor) image sensor as a main component. The imaging part 110 performs the imaging in response to a command from the image processing part 120, and outputs image data obtained by the imaging to the image processing part 120.

The image processing part 120 includes a CPU (Central Processing Unit) 122, a memory 124, an imaging control part 126, a communication interface (I/F) 128, an input/output interface (I/F) 130, and an encoder counter 132. These components are connected through a bus 134 so as to be able to conduct data communication with one another.

The CPU 122 is a processor that performs a main calculation in the image processing part 120. Various programs executed by the CPU 122, the image data imaged by the imaging part 110, and various parameters are stored in the memory 124. Typically, the memory 124 includes a volatile storage device such as a DRAM (Dynamic Random Access Memory) and a nonvolatile storage device such as a flash memory.

The imaging control part 126 controls the imaging of the imaging part 110 according to an internal command from the CPU 122. The imaging control part 126 includes an interface that transmits various commands to the imaging part 110 and an interface that receives the image data from the imaging part 110.

The communication interface 128 transmits and receives various pieces of data to and from the robot control device 200. Typically, the visual sensor 100 and the robot control device 200 are connected to each other through Ethernet (registered trademark), and the communication interface 128 is hardware compliant with Ethernet (registered trademark).

The input/output interface 130 outputs various signals to the outside from the image processing part 120, or input various signals from the outside. Particularly, the input/output interface 130 receives the pulse signal generated by the encoder 14, converts the pulse signal into a digital signal, and outputs the digital signal to the encoder counter 132.

The encoder counter 132 counts the number of pulses included in the pulse signal from the encoder 14. Basically, because the encoder counter 132 operates independently of a calculation cycle of the CPU 122, the encoder counter 132 does not fail to take the number of pulses included in the pulse signal from the encoder 14.

On the other hand, the robot control device 200 includes a calculation processing part 210, a communication interface (I/F) 228, an input/output interface (I/F) 230, an encoder counter 232, a picking control part 240, and a movement control part 250.

The calculation processing part 210 is a processor that performs the calculation to output the command to the robot 300 and the movement mechanism 400 based on the positional information from the visual sensor 100, and the calculation processing part 210 includes a memory 220 that is used to track the workpiece W. The positional information on each workpiece W, which is detected by the measurement processing of the visual sensor 100, is stored in the memory 220. The calculation processing part 210 sequentially updates the positional information on the workpiece W according to the traveling (detected based on the pulse signal from the encoder 14) of the target conveyer.

The communication interface (I/F) 228 transmits and receives various pieces of data to and from the image processing part 120 of the visual sensor 100. Typically, the visual sensor 100 and the robot control device 200 are connected to each other through Ethernet (registered trademark), and the communication interface 228 is hardware compliant with Ethernet (registered trademark).

The input/output interface 230 outputs various signals to the outside from the robot control device 200, or input various signals from the outside. Particularly, the input/output interface 230 receives the pulse signal generated by the encoder 14, converts the pulse signal into the digital signal, and outputs the digital signal to the encoder counter 232.

The encoder counter 232 counts the number of pulses included in the pulse signal from the encoder 14. Basically, because the encoder counter 232 operates independently of the calculation cycle of the calculation processing part 210, the encoder counter 232 does not fail to take the number of pulses included in the pulse signal from the encoder 14.

The picking control part 240 (or grasping control part 240) controls the grasping action of the robot 300 in response to the internal command from the calculation processing part 210. The picking control part 240 includes an interface that transmits a target position on each movable axis of the robot 300 and an interface that receives a current position on the movable axis of the robot 300.

The movement mechanism 400 controls the tracking of the movement mechanism 400 driving the robot 300 in response to the internal command from the calculation processing part 210. The movement mechanism 400 includes an interface that transmits the target position and the target speed of the movement mechanism 400 and an interface that receives the current position on a movement axis of the movement mechanism 400.

D. Problem to be Solved

A problem to be solved will be described below in detail.

Figure 4A:
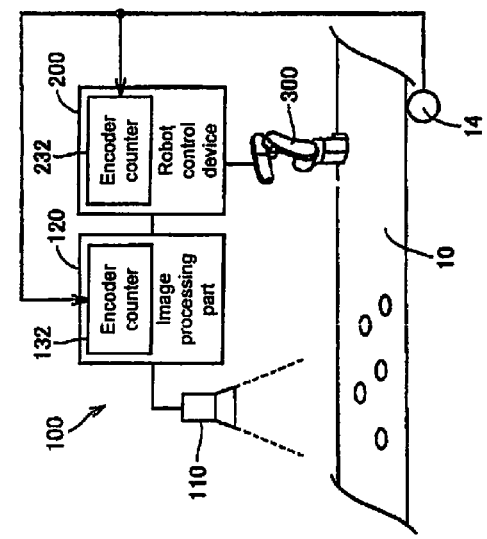
FIGS. 4(a) and 4(b) are views illustrating comparison between the configurations of the conveyer tracking system according to the embodiment of the invention (FIG. 4(b)) and a conveyer tracking system according to a related art (FIG. 4(a)).
Figure 4B:
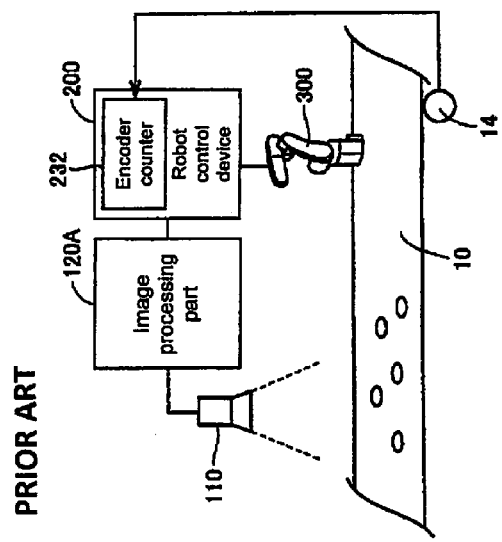

FIGS. 4(a) and 4(b) are views of the configuration of a conveyer tracking system of according to a related art and the configuration of the conveyer tracking system according to the embodiment. That is, FIG. 4(a) illustrates a schematic configuration of the conveyer tracking system according to the related art, and FIG. 4(b) illustrates a schematic configuration of the conveyer tracking system of the embodiment.

In the conveyer tracking system of the related art shown in FIG. 4(a), it is assumed that the pulse signal from the encoder 14 that detects the travel distance of the conveyer 10 is input only to the robot control device 200. In the configuration in FIG. 4(a), based on the pulse signal from the encoder 14, the robot control device 200 provides the imaging command to an image processing part 120A every time the conveyer 10 travels a predetermined distance. In response to the imaging command from the robot control device 200, the image processing part 120A images the subject and performs the measurement processing to the image data obtained by the imaging. The image processing part 120A returns a result of the measurement processing to the robot control device 200.

The imaging timing of the imaging part 110 is set such that at least part of the imaging area of the imaging part 110 in the previous imaging overlaps the imaging area in the current imaging. This is because it is necessary to set a margin to some extent between the imaging areas in the previous imaging and the current imaging such that all the workpieces W flowing on the conveyer 10 can be imaged.

In the case where the system configuration shown in FIG. 4(a) is used, the tracking processing may not be accurately performed when the conveying speed (the line speed) of the conveyer is relatively fast. The reason will be described below with reference to FIGS. 5 and 6.

Figure 6:
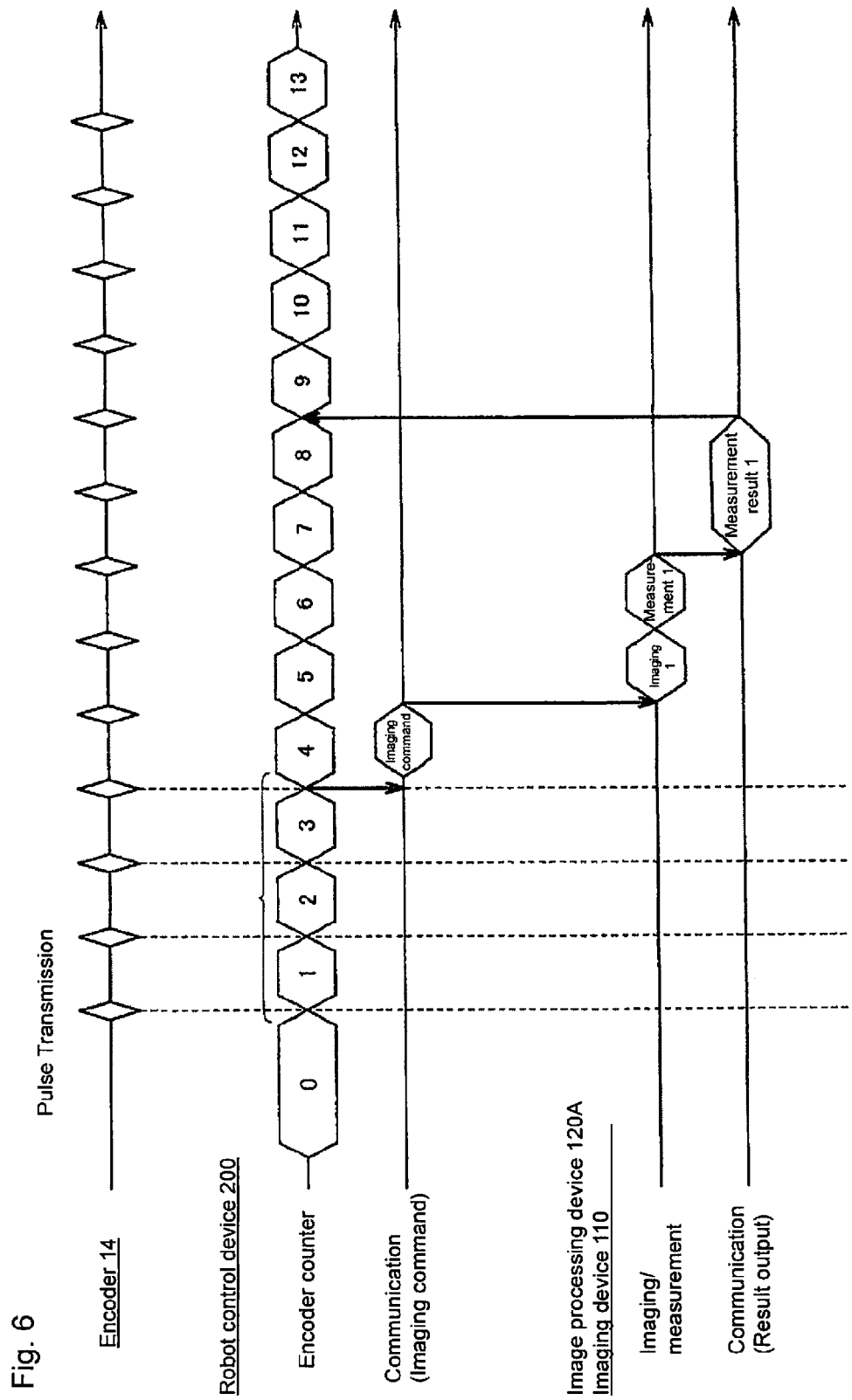
FIG. 6 is a timing chart illustrating the control operation in the tracking system according to the related art.

FIG. 5 is a sequence diagram illustrating the control operation in the tracking system according to the related art. FIG. 6 is a timing chart illustrating the control operation in the tracking system according to the related art.

FIG. 5 illustrates processing in the case where the robot control device 200 issues the imaging command to the imaging part 110 through the image processing part 120A every time the conveyer 10 travels the predetermined distance. Referring to FIG. 5, the calculation processing part 210 of the robot control device 200 determines whether the number of pulses included in the pulse signal from the encoder 14 increases by a predetermined value or more compared with a value of the previous imaging (step S100). That is, it is determined whether the current counter value of the encoder counter 232 increases greater than or equal to a distance corresponding to the imaging timing.

When the number of pulses included in the pulse signal from the encoder 14 reaches a predetermined value or more, the calculation processing part 210 of the robot control device 200 refers to the encoder counter 232 to acquire the current counter value (C0') (step S102). Then, the calculation processing part 210 of the robot control device 200 transmits the imaging command to the image processing part 120A (step S104). The imaging command is transmitted to the image processing part 120A through the network NW. The image processing part 120A causes the imaging part 110 to perform the imaging in response to the imaging command from the robot control device 200 (step S106). The image obtained by the imaging of the imaging part 110 is transmitted to the image processing part 120A. The image processing part 120A performs the measurement processing to the image from the imaging part 110 (step S108). The image processing part 120A transmits, to the robot control device 200, the measurement result (the positional information (X, Y, θ) on each workpiece) obtained by the measurement processing in step S108 (step S110).

The robot control device 200 performs the overlapping removal processing based on the measurement result from the image processing part 120A (step S112). As described above, the imaging timing of the imaging part 110 is controlled such that the imaging areas of continuous pieces of imaging overlap each other. For this reason, the identical workpiece W may be included in a plurality of images. The overlapping removal processing is processing that deletes the acquired overlapped positional information to prevent a tracking trouble caused by the identical workpiece W included in the plurality of images.

The calculation processing part 210 of the robot control device 200 determines whether the positional information on the new workpiece W is acquired (step S114). When the positional information on the new workpiece W is acquired (YES in step S114), the calculation processing part 210 stores the positional information on the new workpiece W in the memory (step S116). The processing is then returned.

At this point, the robot control device 200 deals with the measurement result transmitted from the image processing part 120A in step S110 as the value acquired using the counter value C0' acquired in corresponding step S102. In update processing of the positional information (the coordinate value (X, Y)) on the workpiece W in association with the travel of the conveyer 10, an update amount (ΔX, ΔY) are calculated based on a difference between the counter value C0' and a counter value C1 acquired in update timing. Therefore, it is necessary to accurately reflect the actual imaging timing in the counter value C0', which is correlated with the positional information on each workpiece W and indicates the imaging timing.

However, in the configuration in FIG. 4(a), the counter value C0' acquired in step S102 may not accurately reflect the actual imaging timing. That is, because a delay (the time lag) is generated by the following factors (1) and (2) until the imaging is actually performed after the robot control device 200 transmits the imaging command, the acquired counter value differs from the counter value indicating the original imaging timing when the conveying speed of the conveyer 10 is enhanced. Therefore, an error cannot be ignored in the positioning processing and the tracking processing.

(1) Because the robot control device 200 issues the imaging command after temporarily receiving the pulse signal from the encoder 14, the delay of one cycle of the program executed by the robot control device 200 is generated until the imaging command is actually output after the input timing of the pulse signal.

(2) A transmission delay of the imaging command is generated in the case where the robot control device 200 and the image processing part 120A are connected to each other through a network (such as Ethernet (registered trademark)).

The control operation will more specifically be described with reference to FIG. 6. In a timing chart in FIG. 6, it is assumed that the robot control device 200 issues the imaging command every time the encoder 14 generates three pulses. Assuming that the encoder counter 232 is initialized (counter-reset), the imaging command is output to the image processing part 120A when the encoder counter 232 reaches the counter value of "3". However, whether the calculation processing part 210 of the robot control device 200 reaches the counter value of "3" can be determined after the counter value actually reaches "3", possibly the next pulse is already input in the case where the conveying speed of the conveyer 10 increases relatively. That is, as illustrated in FIG. 6, the encoder counter 232 may have already reached the counter value of "4" at the time the robot control device 200 issues the imaging command.

In the case where the imaging command is transmitted from the robot control device 200 to the image processing part 120A through the network NW, the transmission delay of the imaging command is generated, the imaging of the imaging part 110 and the measurement processing of the image processing part 120A are performed in series, and the measurement result is returned to the robot control device 200 through the network again.

Because of the sequence of pieces of processing, for example, even if the output of the imaging command is set at the timing at which the encoder counter 232 reaches "3", the imaging may actually be performed at the timing at which the encoder counter 232 reaches "5"

The method for eliminating the influence of the delay (the time lag) on the positioning processing and the tracking processing as much as possible is adopted in the visual sensor 100 of the embodiment.

In order to reduce the error due to the delay, it is conceivable to adopt a method for correcting the error by performing an offset of a given amount to the counter value. However, it is necessary to change the offset every time the traveling speed of the conveyer 10 changes.

E. Operation of the Embodiment

The conveyer tracking system of the first embodiment will be described below. In the conveyer tracking system in FIG. 4(b) of the embodiment, it is assumed that the pulse signal from the encoder 14 that detects the travel distance of the conveyer 10 is input to the visual sensor 100 in addition to the robot control device 200. The visual sensor 100 and the robot control device 200 include the encoder counters 132 and 232, respectively. Each of the encoder counters independently counts the pulse in the pulse signal from the encoder 14. Note that the encoder counters 132 and 232 are reset before their operations, and the parameters related to the counting operation are set to the identical values in the encoder counters 132 and 232. Therefore, the counter value counted by the encoder counter 132 and the counter value counted by the encoder counter 232 indicate the identical value in synchronization with each other.

Thus, an environment in which the visual sensor 100 and the robot control device 200 synchronously maintain the counter value is implemented, and the counter value in the imaging performed by the visual sensor 100 is transmitted to the robot control device 200 together with the measurement result (the positional information on each workpiece) obtained by the imaging. In this manner, the visual sensor 100 of the embodiment outputs the counter value indicating the timing at which the imaging is actually performed while correlating the counter value with the measurement result. Therefore, the robot control device 200 can accurately perform the positioning processing and the tracking system processing. In the case where the robot control device 200 performs the overlapping removal processing, the overlapping removal processing can also be accurately performed.

The control operation in the tracking system of the embodiment will be described in detail with reference to FIGS. 7 to 9.

Figure 7:
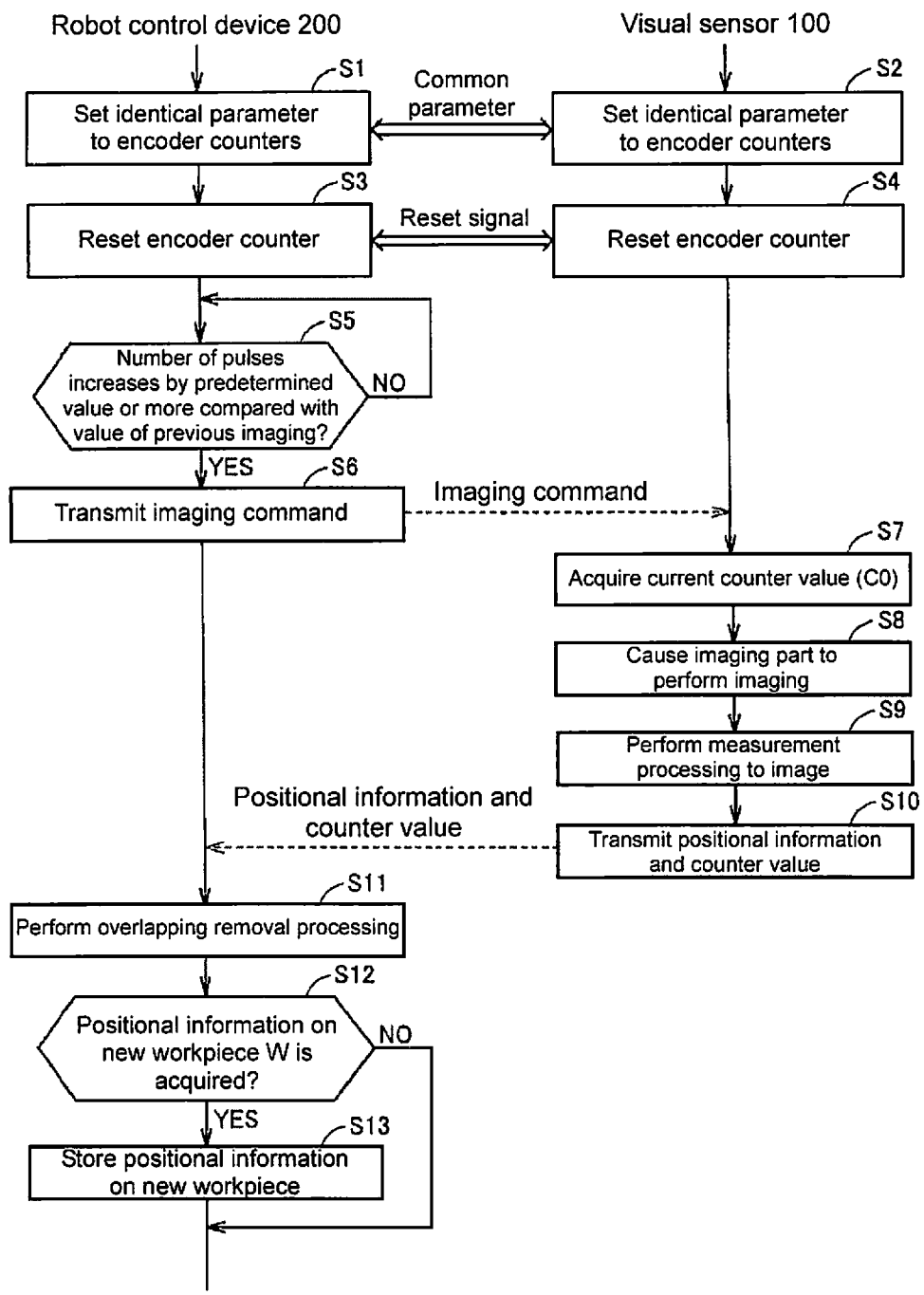
FIG. 7 is a sequence diagram illustrating the control operation in the tracking system according to the first embodiment of the invention.

FIG. 7 is a sequence diagram illustrating the control operation in the tracking system according to the first embodiment of the invention. FIG. 8 is a view illustrating a format example of the measurement result transmitted in the tracking system according to the first embodiment. FIG. 9 is a timing chart illustrating the control operation in the tracking system according to the first embodiment.

Similarly to FIG. 5, FIG. 7 illustrates processing in the case where the robot control device 200 issues the imaging command to the imaging part 110 every time the conveyer 10 travels the predetermined distance.

Referring to FIG. 7, the identical parameters (such as the counter maximum value, the counter minimum value, and the increasing value per pulse) are set to the visual sensor 100 and the robot control device 200 (steps S1 and S2). The encoder counters of the visual sensor 100 and the robot control device 200 are reset (counter-reset) (steps S3 and S4). The setting of the common parameter and the counter reset are performed to the encoder counters, whereby the visual sensor 100 and the robot control device 200 can synchronize the counting operation with respect to the number of pulses included in the pulse signal from the encoder 14.

Then, the calculation processing part 210 of the robot control device 200 determines whether the number of pulses included in the pulse signal from the encoder 14 increases by the predetermined value or more compared with the value of the previous imaging (step S5). That is, it is determined whether the current counter value of the encoder counter 232 increases greater than or equal to a distance corresponding to the imaging timing.

When the number of pulses included in the pulse signal from the encoder 14 reaches the predetermined value or more, the calculation processing part 210 of the robot control device 200 transmits the imaging command to the visual sensor 100 (step S6). The imaging command is transmitted to the visual sensor 100 through the network NW. In response to the imaging command from the robot control device 200, the image processing part 120 of the visual sensor 100 refers to the encoder counter 132 to acquire the counter value (C0) in the imaging (step S7).

Then, the image processing part 120 of the visual sensor 100 causes the imaging part 110 to perform the imaging (step S8). The image obtained by the imaging of the imaging part 110 is transmitted to the image processing part 120. The image processing part 120 performs the measurement processing to the image from the imaging part 110 (step S9). The image processing part 120 transmits, to the robot control device 200, the measurement result (the positional information (X, Y, θ) on each workpiece) obtained by the measurement processing in step S9 together with the counter value C0 acquired in step S7 (step S10).

The robot control device 200 performs the overlapping removal processing based on the measurement result from the image processing part 120 (step S11). The overlapping removal processing is similar to the above-described processing.

The calculation processing part 210 of the robot control device 200 determines whether the positional information on the new workpiece W is acquired (step S12). When the positional information on the new workpiece W is acquired (YES in step S12), the calculation processing part 210 stores the positional information on the new workpiece W in the memory (step S13). The processing is then returned.

In step S10 of the sequence diagram of FIG. 7, the measurement result is transmitted in the format of FIG. 8. FIG. 8 illustrates a data example in the case where three workpieces W matched with the model image are detected.

That is, "3" which is the number of detected workpieces W is stored in the first item, and the pieces of positional information (the X-coordinate value, the Y-coordinate value, and the rotation angle θ) on the three detected workpieces W are stored in the second to tenth items. The counter value indicating the timing at which the image used to generate the detection result is stored in the final item. FIG. 8 illustrates an example in which the imaging is performed at the counter value of "100".

It is easily understood that the format in FIG. 8 is extended according to the number of detected workpieces. In the case where the workpiece W matched with the predetermined model image is not detected, "null" may be transmitted as the detection result.

The more specific control operation in the conveyer tracking system of the embodiment will be described with reference to FIG. 9. In a timing chart in FIG. 9, it is assumed that the robot control device 200 issues the imaging command every time the encoder 14 generates three pulses.

As described above, the common parameters are set to the encoder counters of the visual sensor 100 and the robot control device 200, and the encoder counters are previously initialized (the counter reset). Therefore, in response to the pulse signal generated from the encoder 14, the encoder counters count up the pulse in substantial synchronization with each other.

When the encoder counter 232 reaches the counter value of "3" after the processing is initiated, the imaging command is issued to the visual sensor 100. Similarly to the timing chart in FIG. 6, the encoder counter 232 may have already reached the counter value of "4" at the timing at which the robot control device 200 issues the imaging command. Additionally, the transmission delay is generated in the case where the robot control device 200 transmits the imaging command to the visual sensor 100 through the network NW.

On the other hand, from the viewpoint of the visual sensor 100, the imaging of the imaging part 110 and the measurement processing of the image processing part 120A are performed when the imaging command is received at some sort of timing. In concurrence with the imaging and the measurement processing, the counter value in the imaging is acquired in the visual sensor 100. The visual sensor 100 then transmits the measurement result to the robot control device 200 together with the counter value in the imaging.

Similarly, the robot control device 200 issues the imaging command to the visual sensor 100, and the visual sensor 100 performs the imaging and the measurement processing in response to the imaging command.

As described above, the measurement result is transmitted while the counter value indicating the imaging timing of the visual sensor 100 is added to the measurement result, so that the robot control device 200 can accurately perform the tracking processing based on the counter value corresponding to the measured value.

That is, in the conveyer tracking system of the embodiment, it is not strictly necessary to control the timing at which the robot control device 200 transmits the imaging command (in other words, the imaging command only needs to be transmitted in a cycle according to the conveying speed of the conveyer), and the transmission delay of the measurement result from the visual sensor 100 to the robot control device 200 does not become a problem.

F. Modification of Method for Determining Counter Value in Imaging

Figure 9:
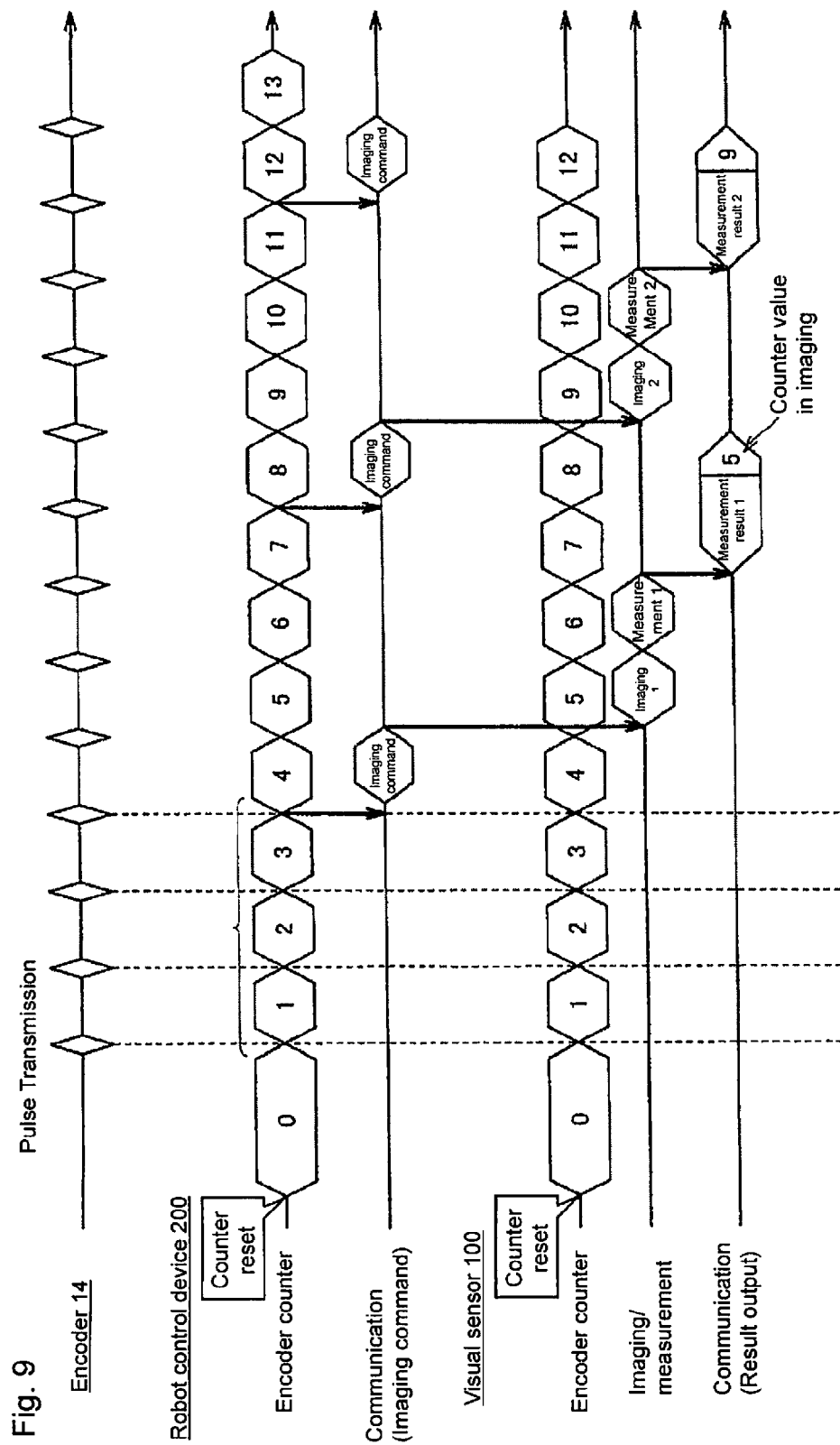
FIG. 9 is a timing chart illustrating the control operation in the tracking system according to the first embodiment of the invention.

In the timing chart in FIG. 9, by way of example, the counter value is acquired before the imaging of the visual sensor 100. However, since the imaging is performed independently of the timing at which the encoder 14 generates the pulse signal, the counter value may be updated during the imaging. Particularly, a possibility of updating the counter value during the imaging increases in the belt conveyer having the higher conveying speed.

Depending on an imaging environment, a period longer than the cycle during which the encoder 14 generates the pulse signal may be necessary for the imaging.

In such cases, the counter values may be acquired at a plurality of timings during the imaging including before the initiation and after the end, and the counter value indicating the imaging timing may be determined based on the plurality of acquired counter values.

Figure 10:
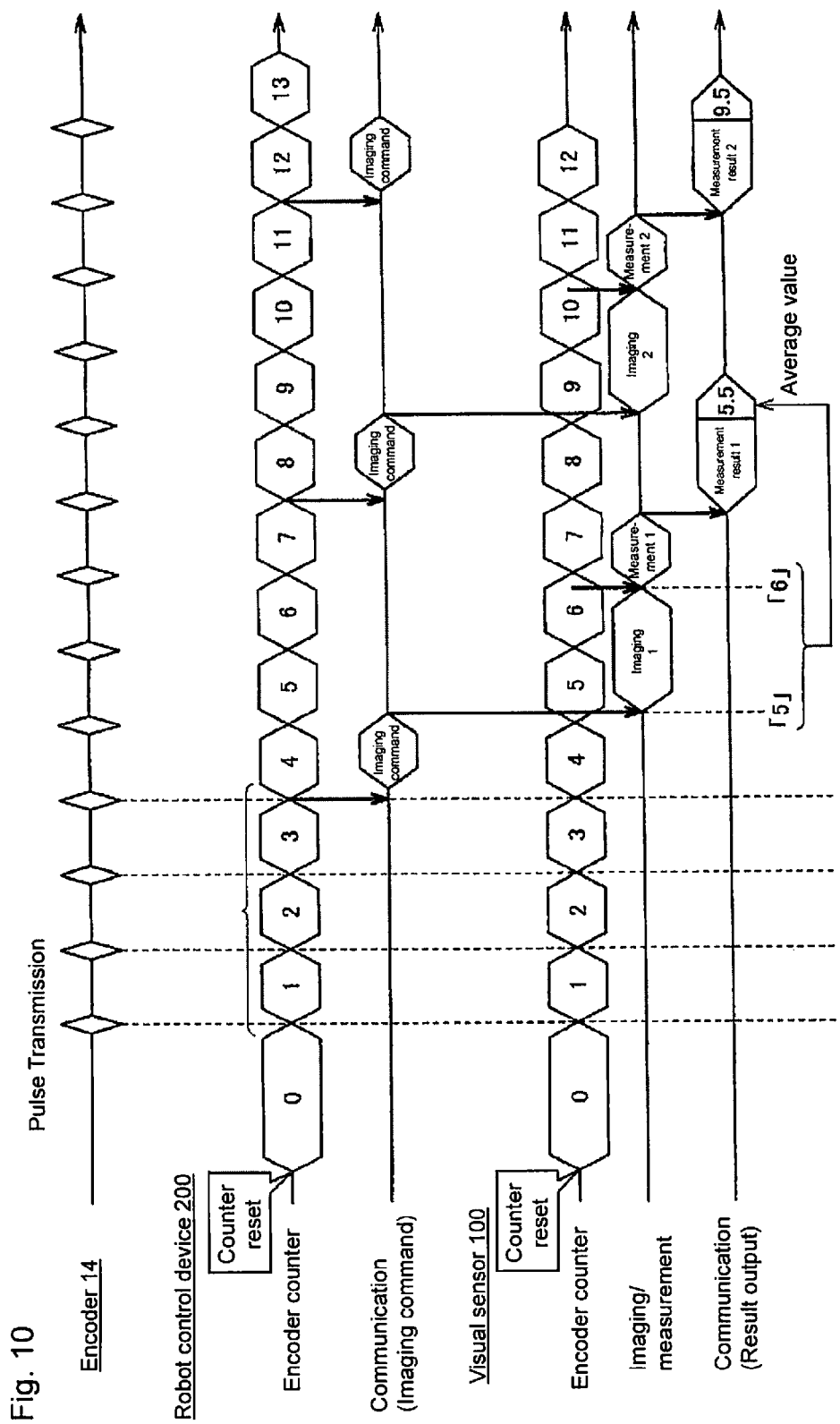
FIG. 10 is a timing chart illustrating a control operation in a tracking system according to a modification of the first embodiment of the invention.

FIG. 10 is a timing chart illustrating control operation in a tracking system according to a modification of the first embodiment of the invention. In the timing chart in FIG. 10, by way of example, the counter values are acquired before and after the imaging and averaged, and the averaged value is dealt with as the counter value in the imaging.

The use of the processing can accurately acquire the counter value indicating the imaging timing even if the time required for the imaging is longer than the cycle during which the pulse signal is generated.

G. Modification of Issue of Imaging Command

As described above, in the conveyer tracking system of the embodiment, it is not strictly necessary to control the timing at which the robot control device 200 transmits the imaging command. Therefore, the visual sensor 100 may internally issue the imaging command instead of a mode in which the robot control device 200 issues the imaging command.

Figure 11:
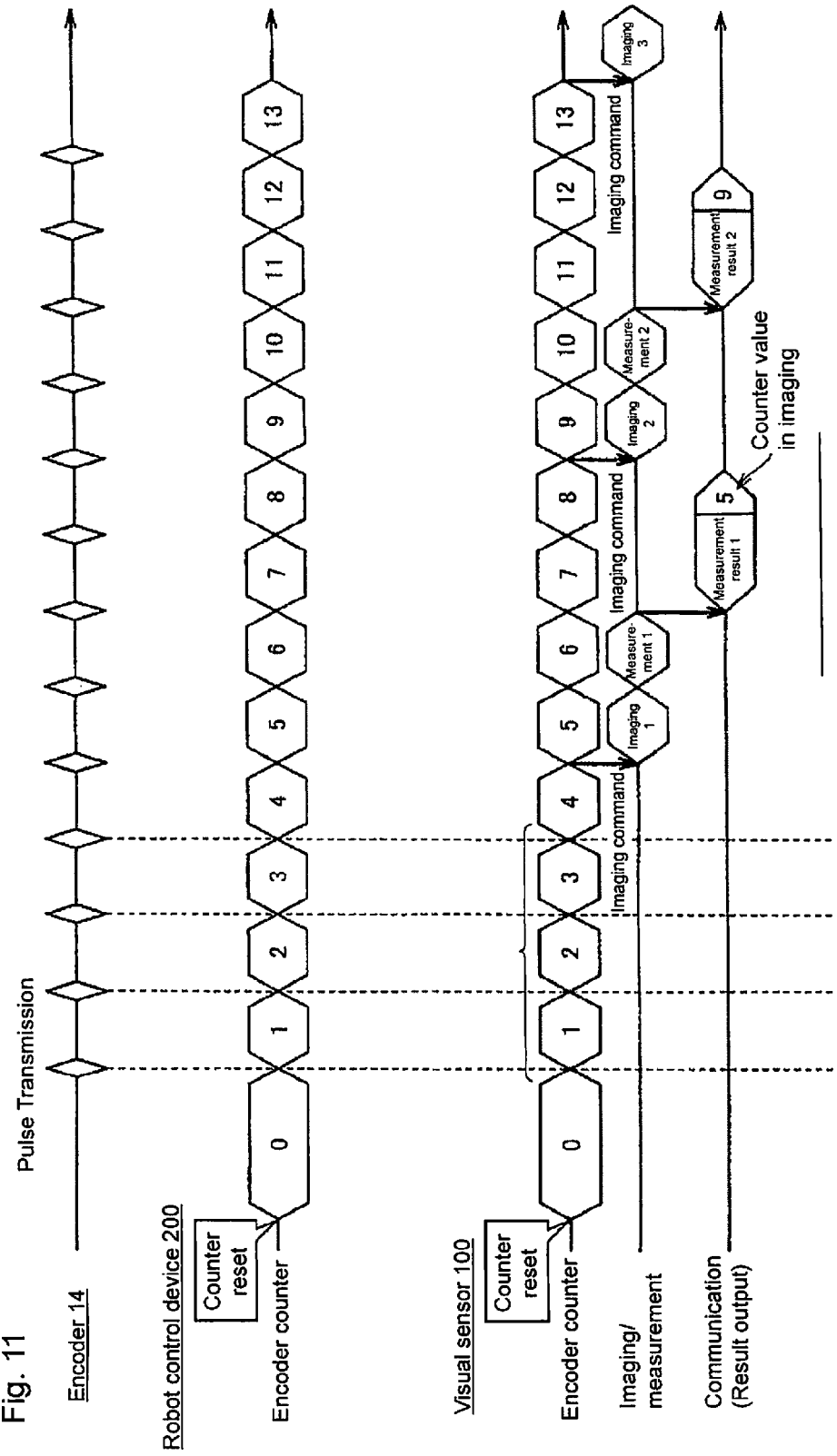
FIG. 11 is a timing chart illustrating a control operation in a tracking system according to another modification of the first embodiment of the invention.

FIG. 11 is a timing chart illustrating control operation in a tracking system according to another modification of the first embodiment of the invention. In the example in FIG. 11, the visual sensor 100 refers to the counter value of the encoder counter 132, and internally issues the imaging command every time the encoder 14 generates three pulses.

From the viewpoint of the robot control device 200, because the counter value indicating the timing at which the imaging is performed can be acquired, the positioning processing and the tracking processing of the workpiece can be performed without any difficulty even if the configuration in FIG. 11 is used. Because the imaging command is not transmitted through the network NW, a load on the network NW can be advantageously reduced.

H. Processing in Robot Control Device

The processing in robot control device 200 will be described below.

Figure 12:
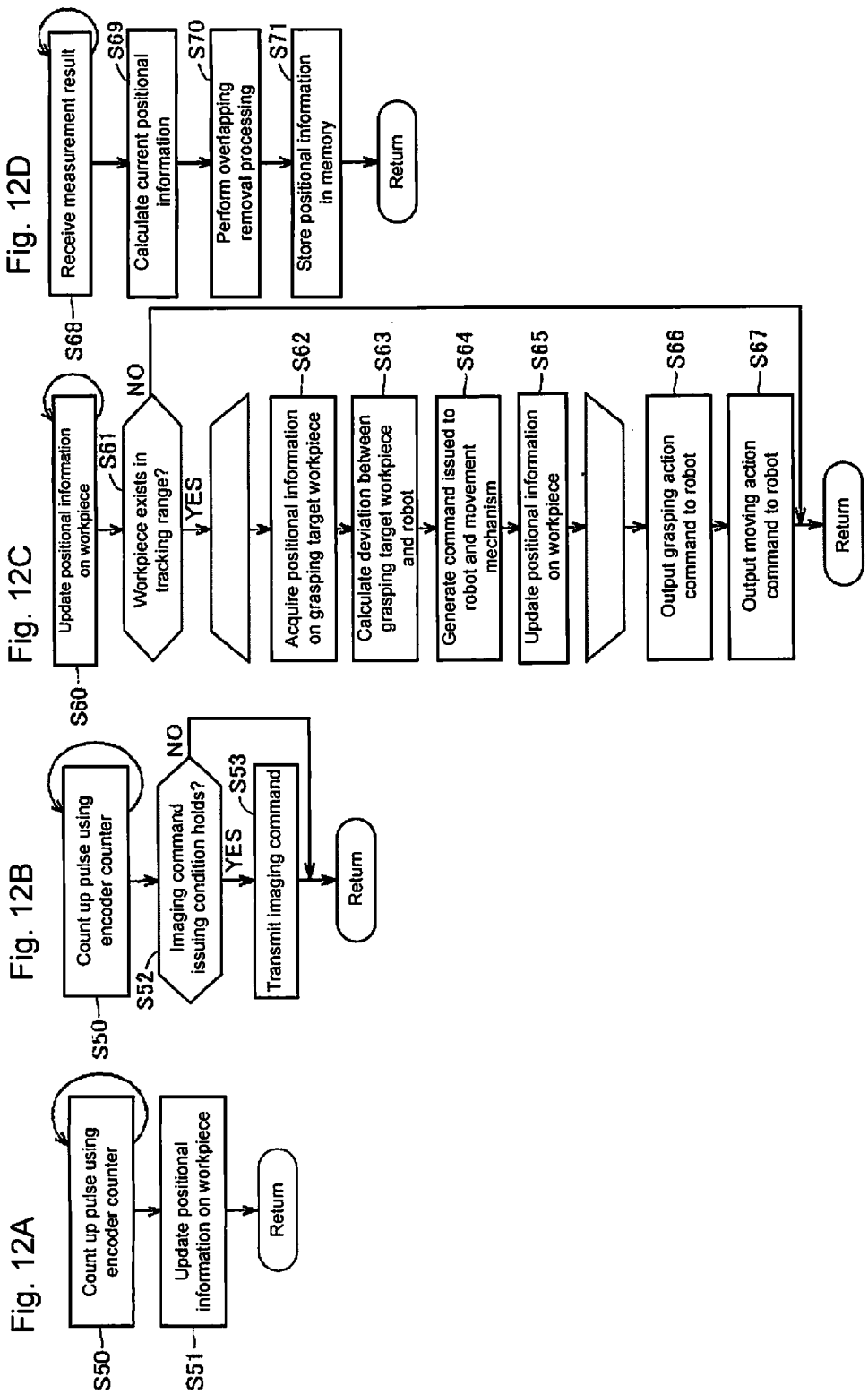
FIGS. 12(a) to 12(d) are flowcharts illustrating processing in a robot control device according to the first embodiment of the invention.

FIGS. 12(*a*) to 12(*d*) are flowcharts illustrating the processing in the robot control device 200 according to the first embodiment of the invention. FIGS. 12(*a*) to 12(*d*) illustrate main portions of processing performed in the robot control device 200. However, the processing in the robot control device 200 is not limited to the portions of processing in FIG. 12.

FIG. 12(*a*) illustrates the processing that is performed when the encoder 14 generates the pulse signal. More specifically, the encoder 14 generates the pulse signal and the encoder counter 232 counts up the pulse (step S50), whereby the processing in FIG. 12(*a*) is activated. When the encoder counter 232 counts up the pulse, the positional information on each workpiece stored in the memory of the robot control device 200 is updated (step S51). The positional information updating method is as follows.

As illustrated in FIG. 2, it is assumed that the workpiece is conveyed in the X-direction, and that an origin in the X-direction is the right end in the tracking range of the robot 300. At this point, assuming that ($\Delta Mx$, $\Delta My$) is the travel distance (a moving vector) of the conveyer per pulse of the encoder 14, and that (X0, Y0, θ0) is the pre-update positional information on the workpiece W, the post-update positional information becomes (X0−$\Delta Mx \times n$, Y0−$\Delta My \times n$, θ0) when n pulses are input. That is, the value that is obtained by multiplying a unit travel distance per pulse on the conveyer by the number of pulses becomes the travel distance ($\Delta Mx \times n$, $My \times n$) of the workpiece W. When the workpiece W moves in the direction toward the origin, the positional information on the workpiece is updated by the travel distance (the moving vector).

The robot control device 200 waits until the encoder counter 232 newly counts up the pulse.

FIG. 12(b) also illustrates the processing that is performed when the encoder 14 generates the pulse signal. More specifically, the encoder 14 generates the pulse signal and the encoder counter 232 counts up the pulse (step S50), whereby the processing in FIG. 12(b) is activated. When the encoder counter 232 counts up the pulse, whether an imaging command issuing condition holds is determined. For example, it is determined whether the number of pulses included in the pulse signal from the encoder 14 increases by the predetermined value or more compared with the value of the previous imaging. When the imaging command issuing condition holds (YES in step S50), the robot control device 200 transmits the imaging command to the visual sensor 100.

FIG. 12(c) illustrates the grasping operation performed by the robot 300. The flow in FIG. 12(c) is activated when the positional information on the workpiece is updated (step S60). More specifically, when the positional information on the workpiece is updated, whether the workpiece W exists in the tracking range of the robot 300 is determined (step S61). When the workpiece W exists in the tracking range of the robot 300 (YES in step S61), the control of the action to grasp the workpiece W by the robot 300 is initiated. Specifically, the acquisition of the positional information on the grasping target workpiece existing in the tracking range (step S62), the calculation of a deviation between the grasping target workpiece and the robot 300 (step S63), generation of the commands issued to the robot 300 and the movement mechanism 400 based on the deviation calculated in step S63 (step S64), and the update of the positional information on the workpiece W (step S65) are repeated. When the robot 300 moves to the position where the robot 300 can grasp the workpiece W, the robot control device 200 issues a grasping action command to the robot 300 (step S66). Then, the robot control device 200 issues a moving action command to the robot 300, which is in the grasping state, to move the grasped workpiece W to the target position (step S67). The processing is then returned.

The processing in FIG. 12(d) is activated when another piece of positional information is received. More specifically, the current positional information is calculated (step S69), and the overlapping removal processing is performed (step S70). Then, the positional information is stored in the memory (step S71).

As to the method in step S69 for calculating the current positional information on the workpiece W, the difference between the counter value at the time of imaging and the counter value at each time point is calculated, and the value that is obtained by multiplying the difference by the unit travel distance per pulse on the conveyer becomes a correction amount. The current positional information is calculated by applying the correction amount to the measurement result (the positional information on the workpiece received from the visual sensor 100).

Figure 13:
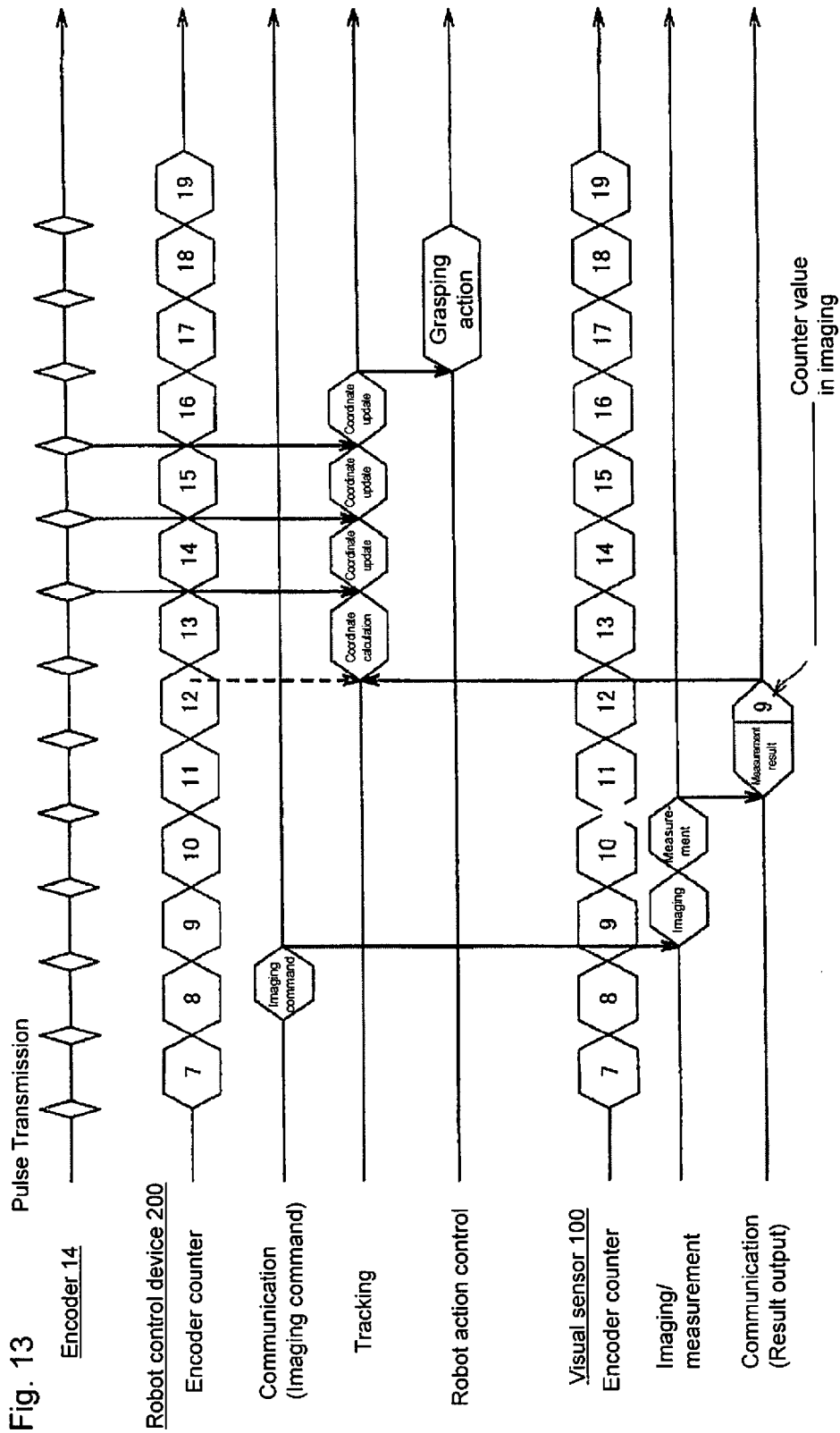
FIG. 13 is a timing chart illustrating the general control operation in the tracking system according to the first embodiment of the invention.

FIG. 13 is a timing chart illustrating the whole control operation in the tracking system according to the first embodiment of the invention. Referring to FIG. 13, for example, it is assumed that the imaging command is issued at the timing at which the encoder counter 232 of the robot control device 200 reaches the counter value of "7". The imaging command is transmitted to the visual sensor 100 to perform the imaging processing and the measurement processing. The measurement result is transmitted to the robot control device 200 together with the counter value of "9" that is the counter value in the imaging of the encoder counter 132 of the visual sensor 100.

When receiving the measurement result from the visual sensor 100, the robot control device 200 compares the correlated counter value in the imaging (in this example, "9") and the current counter value (in this example, "12") after the overlapping removal processing and the like, and corrects the measurement result by the counter value of "3" that is the difference (coordinate calculation). Additionally, the robot control device 200 updates the stored positional information (the coordinate position of each workpiece) every time the encoder counter 232 counts up the pulse (coordinate update).

Thereafter, when the target workpiece W enters the tracking range of the robot 300, the robot control device 200 issues the grasping action command to the robot 300. When the grasping action of the robot 300 is completed, the positional information on the workpiece stored in the robot control device 200 is deleted.

The conveyer tracking of the embodiment is performed by the above processing procedure.

I. Advantage

According to the embodiment, the visual sensor 100 (the image processing part 120) directly receives the input of the pulse signal from the encoder 14, the imaging and the measurement processing performed to the image obtained by the imaging are not influenced by the program execution cycle of the robot control device 200.

The counter value in the imaging can be accurately acquired in the visual sensor 100 (the imaging part 110) even if the robot control device 200 issues the imaging command at any timing. Therefore, the tracking processing and the control of the robot 300 can be accurately performed even if the delay time that cannot be ignored is generated between the imaging command and the actual imaging.

Even if the conveyer speed changes, it is not necessary to adjust the parameter related to the counting operation according to the conveyer speed, since the counter value in the imaging can be accurately acquired.

Second Embodiment

In the first embodiment, the pulse signal is input from the encoder 14 to both the visual sensor 100 and the robot control device 200, and the main bodies of the visual sensor 100 and the robot control device 200 count the number of pulses included in the pulse signal using the encoder counters 132 and 232 to which the identical parameters are set, whereby the visual sensor 100 and the robot control device 200 maintain the travel distance (the counter value) of the conveyer in synchronization with each other. On the other hand, in a second embodiment, a configuration is illustrated in which the visual sensor and the robot control device maintain the travel distance (the counter value) of the conveyer in synchronization with each other through the network.

Figure 14:
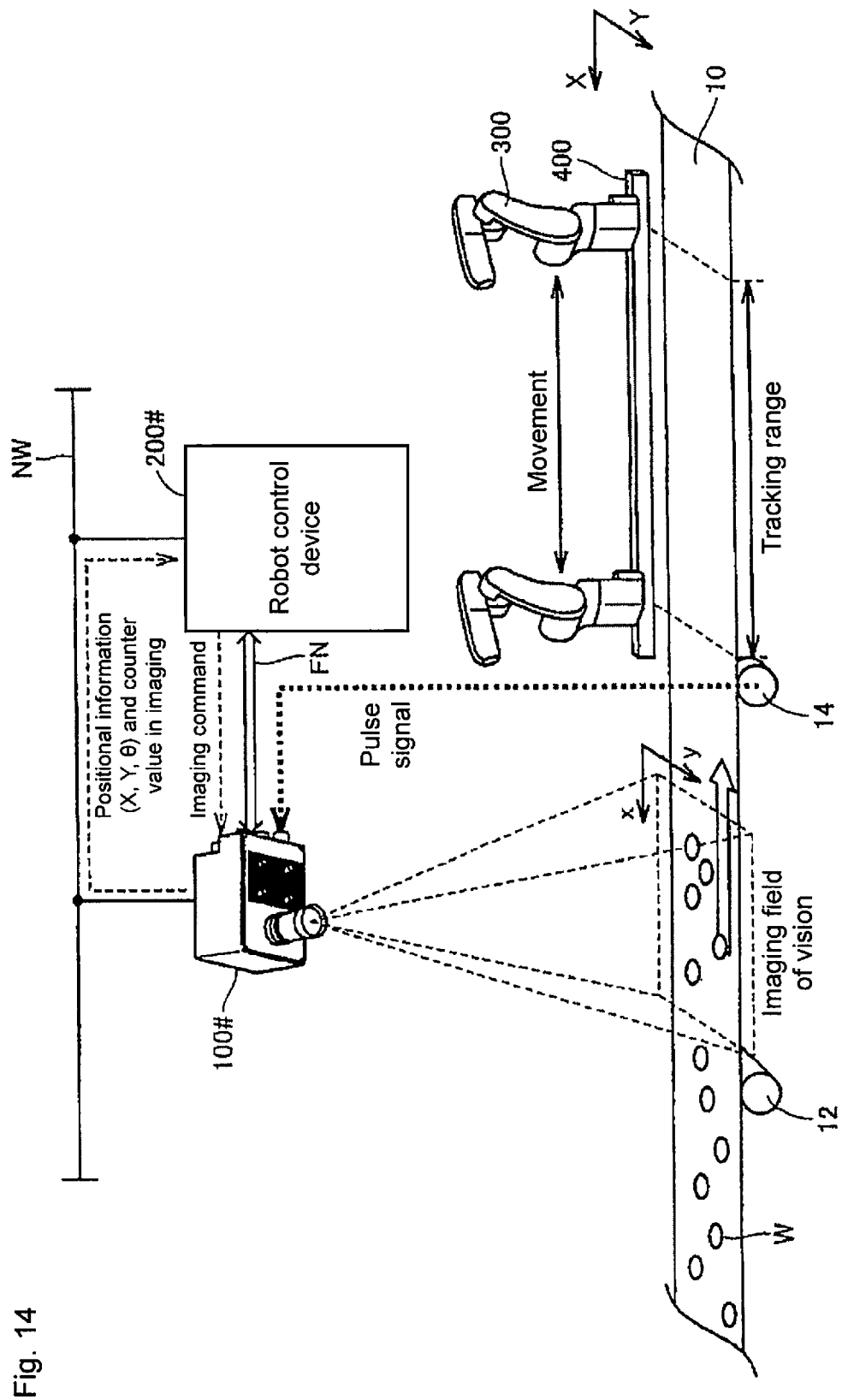
FIG. 14 is a view illustrating positioning processing and tracking processing in a conveyer tracking system using a visual sensor according to a second embodiment of the invention.

FIG. 14 is a view illustrating positioning processing and tracking processing in a conveyer tracking system using a visual sensor according to the second embodiment of the invention. Referring to FIG. 14, the conveyer tracking system using the visual sensor according the second embodiment differs from the conveyer tracking system in FIG. 2 using the visual sensor according the first embodiment in that the pulse signal is input from the encoder 14 only to a visual sensor 100# and that a field network FN is provided between the visual sensor 100# and a robot control device 200#. Because other configurations are similar to those of the first embodiment, a different point will mainly be described below.

Figure 15:
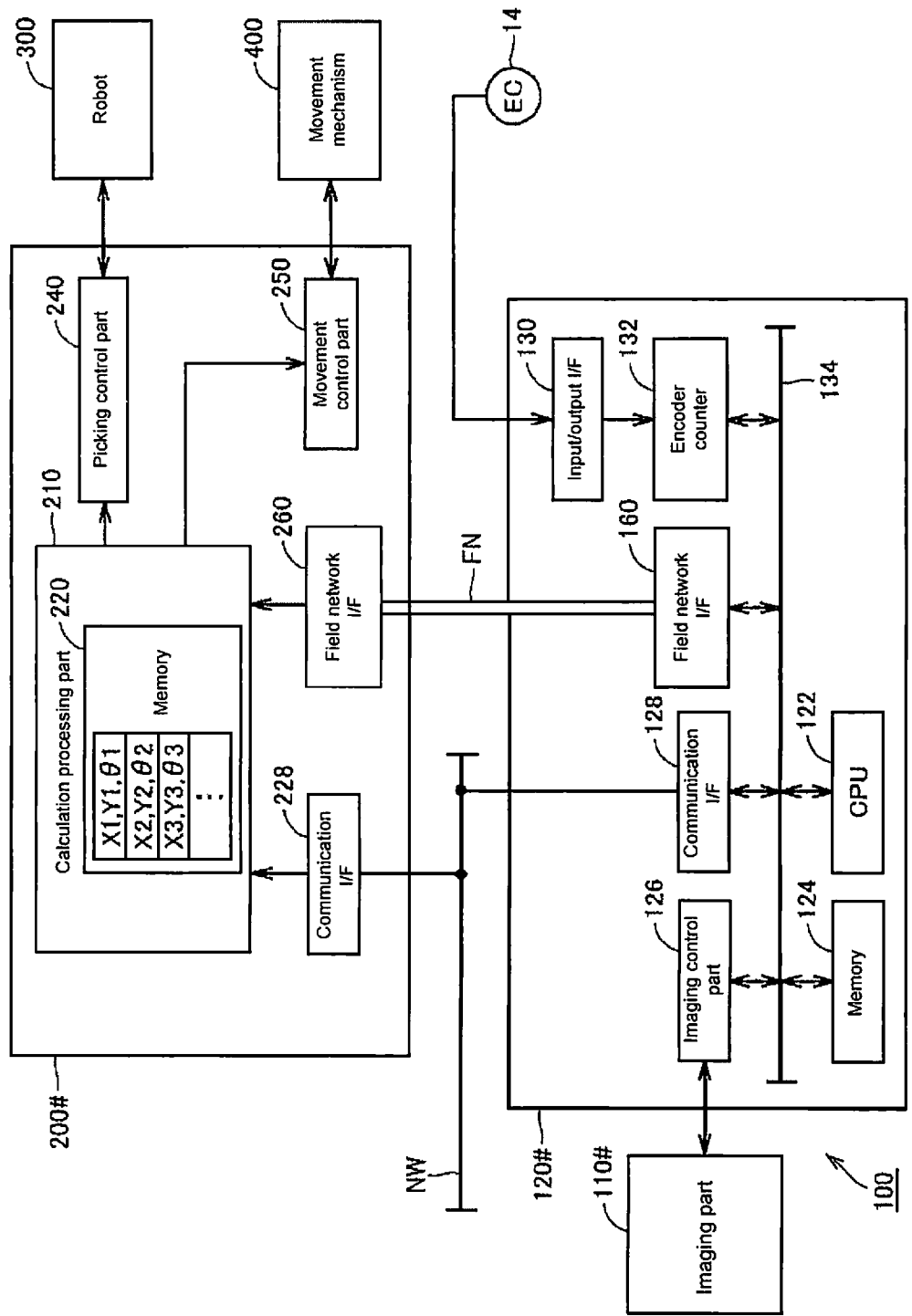
FIG. 15 is a schematic diagram illustrating a hardware configuration of the conveyer tracking system using the visual sensor according to the second embodiment of the invention.

FIG. 15 is a schematic diagram illustrating a hardware configuration of the conveyer tracking system using the visual sensor according to the second embodiment of the invention. Referring to FIG. 15, an image processing part 120# constituting the visual sensor 100# of the second embodiment further includes a field network interface (I/F) 160 compared with the image processing part 120 in FIG. 3. Compared with the robot control device 200 in FIG. 3, the robot control device 200# of the second embodiment is provided with a field network interface (I/F) 260 instead of the encoder counter 232 and the input/output interface (I/F) 230. Because other configurations are similar to those of the first embodiment, a different point will mainly be described below.

The counter value counted by the encoder counter 132 of the image processing part 120# is shared by image processing part 120# constituting the visual sensor 100# and the robot control device 200# through the field network FN.

Typically, various industrial Ethernets (registered trademark) can be used as the field network FN. Examples of the industrial Ethernets (registered trademark) include EtherCAT (registered trademark), Profinet IRT, MECHATROLINK (registered trademark)-III, Powerlink, SERCOS (registered trademark)-III, and CIP Motion, and any industrial Ethernet may be used as the field network FN. A field network other than the industrial Ethernet (registered trademark) may also be used. For example, in the case where motion control is not performed, DeviceNet and CompoNet/IP (registered trademark) may be used. In the embodiment, typically, EtherCAT (registered trademark) that is the industrial Ethernet (registered trademark) is used as the field network FN.

The general field network is configured such that the delay time related to the transmission and the reception is kept constant, and the delay time can be suppressed to several nanoseconds. The delay time is sufficiently small compared with the delay (the time lag) until the imaging is actually performed after the robot control device 200 transmits the imaging command, and it can be assumed that the visual sensor 100# and the robot control device 200# substantially maintain the count value in synchronization with each other.

Unlike the first embodiment, it is not necessary to provide the encoder counters to which the common parameters are set in the visual sensor 100# and the robot control device 200#. Therefore, the two devices can maintain the counter value in synchronization with each other with a simpler configuration. That is, a travel distance obtaining unit that synchronously obtaining the travel distance of the conveyer 10 in the conveying route by both of the visual sensor 100 and the robot control device 200 is implemented by the counter, which is provided in the visual sensor 100 or the robot control device 200 to count the number of pulses in the pulse signal, and the field network FN through which the sensor 100 and the control device 200 maintain the counter value of the counter in synchronization with each other.

Even if the delay time in the field network FN cannot be ignored, the delay time in the field network FN is controlled so as to be kept constant. Therefore, the devices can maintain the counter value of the counter in synchronization with each other by the following method.

Figure 16:
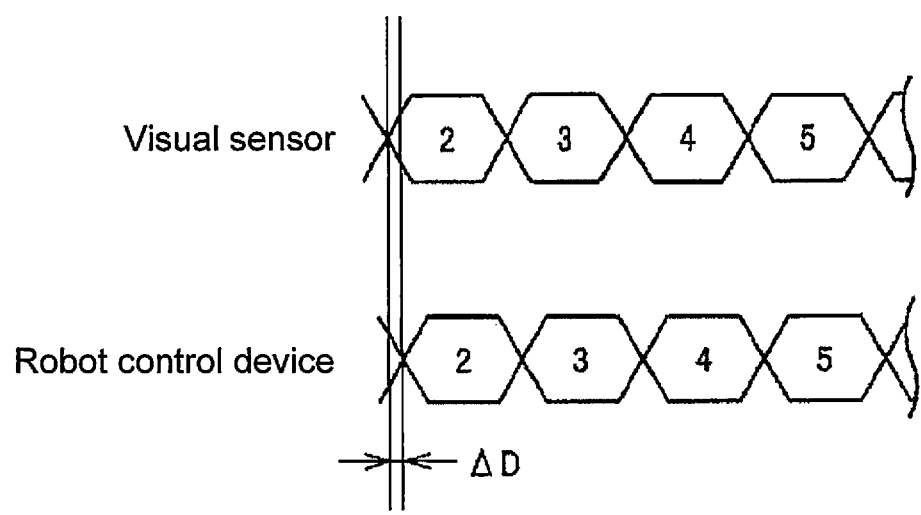
FIG. 16 is a view illustrating an influence of a delay time in a field network according to the second embodiment of the invention.

FIG. 16 is a view illustrating an influence of the delay time in the field network FN according to the second embodiment of the invention. Referring to FIG. 16, for example, it is assumed that the counter value updated by the visual sensor 100# is transmitted to the robot control device 200# with a delay time $\Delta D$. Because the delay time $\Delta D$ is basically predicted to be constant, a countermeasure to shift control timing is conceivable in consideration of the delay time $\Delta D$.

For example, when the control operation initiated by the visual sensor 100# based on the counter value is delayed by the delay time $\Delta D$, the delay time $\Delta D$ between the visual sensor 100# and the robot control device 200# can be substantially canceled.

In the case where the delay time $\Delta D$ is longer than the counter value update cycle, a correction amount (a counter correction value) that is obtained by multiplying a cycle of the pulse included in the pulse signal from the encoder 14 by the delay time $\Delta D$ may be added to the counter value and used in the control.

In the second embodiment, by way of example, the visual sensor 100# becomes a host of the field network FN while the robot control device 200# becomes a slave of the field network FN. Alternatively, the relationship between the host and the slave may be reversed. In this case, the pulse signal from the encoder 14 is input only to the side of the robot control device 200#, and the encoder counter is provided in the robot control device 200#.

Third Embodiment

A support device 600 connected to the visual sensor 100 and the robot control device 200 through the network NW will be described below.

Figure 17:
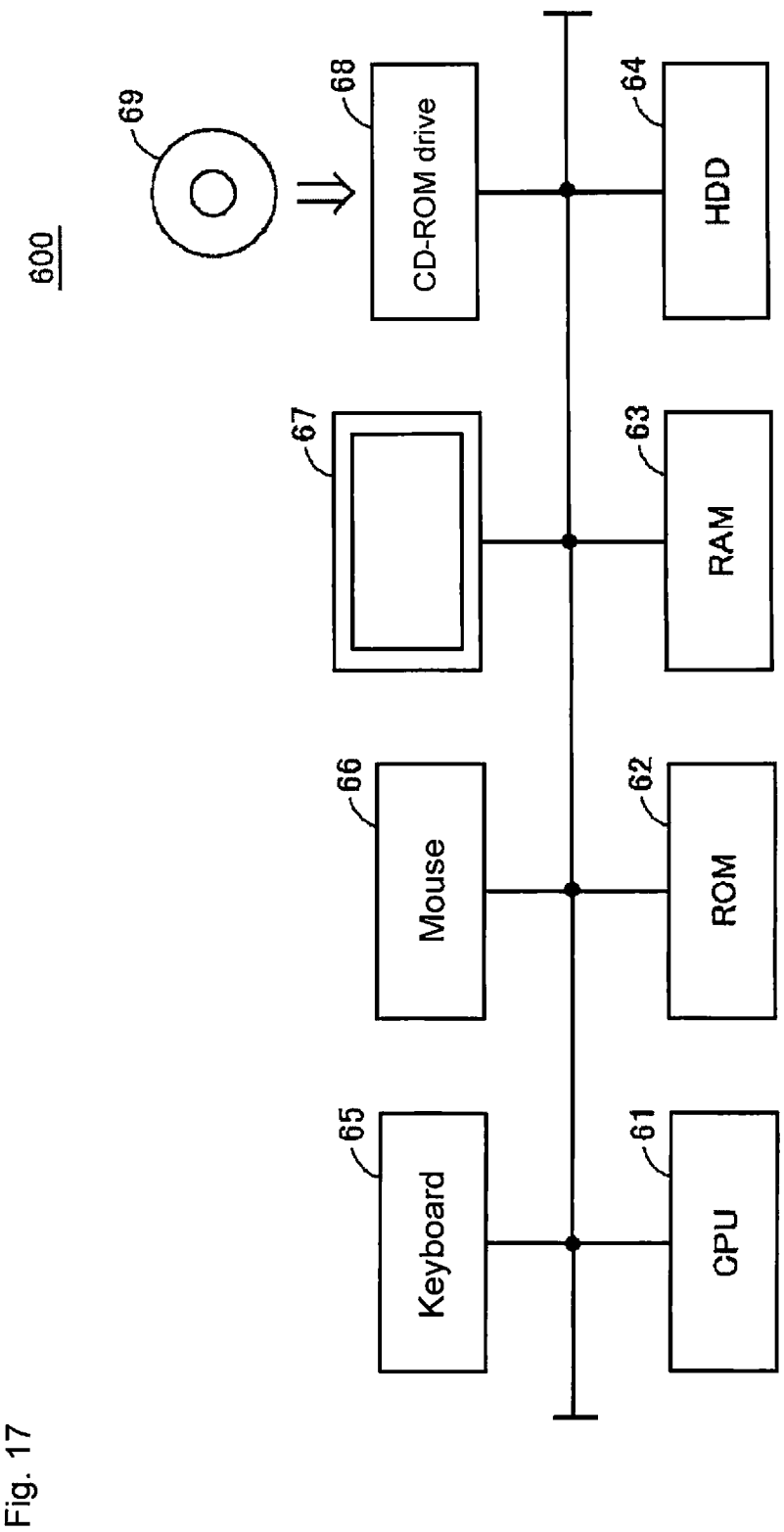
FIG. 17 is a schematic diagram illustrating a hardware configuration of a support device according to a third embodiment of the invention.

FIG. 17 is a schematic diagram illustrating a hardware configuration of the support device 600 according to a third embodiment of the invention. Typically, the support device 600 includes a general-purpose computer. Preferably, a laptop personal computer having excellent portability is used from the viewpoint of maintenance.

Referring to FIG. 17, the support device 600 includes a CPU 61 that executes various programs including an OS, a ROM (Read Only Memory) 62 in which BIOS and various pieces of data are stored, a memory RAM 63 that provides a work area in which the data necessary to execute the program in the CPU 61 is stored, and a hard disk (HDD) 64 in which the program executed in the CPU 61 is stored in a nonvolatile manner.

The support device 600 also includes a keyboard 65 and a mouse 66, which receive the operation from the user, and a monitor 67 that presents information to the user.

As described later, various programs executed by the support device 600 are distributed while stored in a CD-ROM 69. The program stored in the CD-ROM 69 is read by a CD-ROM (Compact Disk-Read Only Memory) drive 68, and stored in the hard disk (HDD) 64. Alternatively, the program may be downloaded from an upper-level host computer through the network.

As described above, because the support device 600 is configured by the general-purpose computer, the detailed description is omitted.

The support device 600 conducts data communication with both the visual sensor 100 and the robot control device 200, so that the support device 600 can collect various pieces of data. Therefore, the support device 600 of the embodiment is configured to collect, from the visual sensor 100, the image which becomes the measurement processing target in the adjustment.

In the case where the image that becomes the measurement processing target is collected from the visual sensor 100, each image is stored while correlated with the corresponding counter value and measured value (such as the coordinate information and the angle information). These pieces of information are transmitted from the visual sensor 100 to the support device 600 through the network NW. The pieces of information are stored in the hard disk 64 of the support device 600.

Particularly, the image and the measurement result are stored with the corresponding counter value as a key while correlated with each other, which allows the necessary image and measurement result to be easily searched using the counter value corresponding to the desired timing.

The following function can be provided by preparing a database for the image and the measurement result. That is, in the robot 300, the robot operation (the positioning processing and the tracking processing) is stored while correlated with the counter value, which allows the robot operation to be correlated with the corresponding image processing. In this manner, for example, in the case where the grasping operation is unsuccessfully performed, the image and the measurement result of the workpiece that is the grasping target can be reproduced on the support device 600 to pursue the cause of failure. Therefore, the cause of trouble can be more easily analyzed.

It is noted that the disclosed embodiment are illustrative in every aspect, but not restrictive. The scope of the invention is indicated not by the above description but by the claims, and all the changes within the meaning and range equivalent to the claims are also included in the invention.

EXPLANATION OF REFERENCE NUMERALS

10 conveyer
12 driving roller
14 encoder
30 discharging device
61, 122 CPU
63 RAM
64 hard disk
65 keyboard
66 mouse
67 monitor
68 drive
69 CD-ROM
100 visual sensor
110 imaging part
120, 120A image processing part
124, 220 memory
126 imaging control part
128, 228 communication interface
130, 230 input/output interface
132, 232 encoder counter
134 bus
200 robot control device
210 calculation processing part
240 picking control part
250 movement control part
300 robot
400 movement mechanism
500 operation display device
600 support device
2100 teaching pendant
FN field network
NW network
W workpiece

The invention claimed is:

1. An image processing apparatus in an image processing system comprising an image sensor, the image processing apparatus and a robot control processor, the robot control processor controlling a robot having an arm grasping workpieces on a conveying route downstream from an imaging area, wherein the image sensor is connected to the image processing apparatus and captures an image of workpieces conveyed on a conveyer in the imaging area, the image processing apparatus comprising:
an input/output interface;
a communication interface; and
a processor coupled to the input/output interface and the communication interface, the processor configured to execute a program, wherein the processor is configured with the program to perform operations comprising:
receiving a signal from an encoder device using the input/output interface, the signal indicating a travel distance of the conveyer in the conveying route; and
communicating with the robot control processor using the communication interface;
the processor is further configured to execute the program to perform operations as:
a positional information acquisition unit that processes the image captured by the image sensor and thereby acquires positional information on a region corresponding to a pre-registered workpiece in the image;
a travel distance obtaining unit that maintains the travel distance of the conveyer in the conveying route in synchronization with the robot control processor based on the signal indicating the travel distance received from the encoder device via the input/output interface;
an initiating unit that initiates the capturing by the image sensor in response to an imaging command; and
a transmission unit that transmits, to the robot control processor via the communication interface, the positional information and the travel distance upon the capturing of the image used to acquire the positional information,
the signal indicating the travel distance of the conveyer in the conveying route is a pulse signal,
the pulse signal is configured to be input to the image processing apparatus and the robot control processor,
the processor is further configured with the program to perform operations such that the travel distance obtaining unit includes a first counter that counts the number of pulses included in the pulse signal,
an identical parameter is set with respect to counting between the first counter and a second counter, the second counter used by the robot control processor to count the number of pulses included in the pulse signal, and the image sensor and the robot control processor synchronously maintain a same count value as a result thereof.

2. The image processing apparatus according to claim 1, wherein the positional information includes a coordinate value in which the region corresponding to the pre-registered workpiece in the image is expressed in a coordinate system of the robot.

3. The image processing apparatus according to claim 2, wherein the positional information further includes a rotation angle of the region corresponding to the pre-registered workpiece in the image, the rotation angle being based on an attitude of the pre-registered workpiece.

4. The image processing apparatus according to claim 1, wherein the processor is further configured with the program to perform operations such that the first counter and the second counter are reset before the counting of the number of pulses included in the pulse signal is started.

5. The image processing apparatus according to claim 1, wherein the processor is further configured with the program to perform operations such that the travel distance upon the capturing of the image used to acquire the positional information is indicated by a counter value of the first counter.

6. The image processing apparatus according to claim 1, wherein the image processing apparatus is configured to receive the imaging command from the robot control processor using the communication interface.

7. An image processing system comprising:
an image sensor that is disposed in a position relative to a conveyor, wherein the image sensor captures an image of workpieces conveyed on the conveyer in an imaging area;
a robot control processor that controls a robot having an arm grasping the workpieces, the robot being disposed downstream of the imaging area of the image sensor in a conveying route of the workpieces on the conveyor; and
an image processing apparatus that is connected to the image sensor and the robot control processor, wherein the image processing apparatus includes:
an input/output interface;
a communication interface; and
a processor coupled to the input/output interface and the communication interface, the processor configured to execute a program, wherein the processor is configured with the program to perform operations comprising:
receiving a signal from an encoder device using the input/output interface, the signal indicating a travel distance of the conveyer in the conveying route; and
communicating with the robot control processor using the communication interface;
the processor is further configured to execute the program to perform operations as:
a positional information acquisition unit that processes the image captured by the image sensor and thereby acquires positional information on a region corresponding to a pre-registered workpiece in the image;
a travel distance obtaining unit that maintains the travel distance of the conveyer in the conveying route in synchronization with the robot control processor based on the signal indicating the travel distance received from the encoder device via the input/output interface;
an initiating unit that initiates the capturing by the image sensor in response to an imaging command; and
a transmission unit that transmits, to the robot control processor via the communication interface, the positional information and the travel distance upon the capturing of the image used to acquire the positional information,
the signal indicating the travel distance of the conveyer in the conveying route is a pulse signal,
the pulse signal is configured to be input to the image processing apparatus and the robot control processor,
the processor is further configured with the program to perform operations such that the travel distance obtaining unit includes a first counter that counts the number of pulses included in the pulse signal,
an identical parameter is set with respect to counting between the first counter and a second counter, the second counter used by the robot control processor to count the number of pulses included in the pulse signal, and
the image sensor and the robot control processor synchronously maintain a same count value as a result thereof.

8. The image processing system according to claim 7, wherein the positional information includes a coordinate value in which the region corresponding to the pre-registered workpiece in the image is expressed in a coordinate system of the robot.

9. The image processing system according to claim 8, wherein the positional information further includes a rotation angle of the region corresponding to the pre-registered workpiece in the image, the rotation angle being based on an attitude of the pre-registered workpiece.

10. The image processing system according to claim 7, wherein the processor is further configured with the program to perform operations such that the first counter and the second counter are reset before the counting of the number of pulses included in the pulse signal is started.

11. The image processing system according to claim 8, wherein the processor is further configured with the program to perform operations such that the travel distance upon the capturing of the image used to acquire the positional information is indicated by a counter value of the first counter.

12. The image processing system according to claim 7, wherein the image processing apparatus is configured to receive the imaging command from the robot control processor using the communication interface.

13. An image processing system comprising:
an image sensor that is disposed in a position relative to a conveyor, wherein the image sensor captures an image of workpieces conveyed on the conveyer in an imaging area;
a robot control processor that controls a robot having an arm grasping the workpieces, the robot being disposed downstream of the imaging area of the image sensor in a conveying route of the workpieces on the conveyor; and
an image processing apparatus that is connected to the image sensor and the robot control processor, wherein the image processing apparatus includes:
an input/output interface that receives a signal indicating a travel distance of the conveyer in the conveying route from an encoder device;
a communication interface that communicates with the robot control processor;
means for processing the image captured the image sensor and thereby acquiring positional information on a region corresponding to a pre-registered workpiece in the image;

means for maintaining the travel distance of the conveyer in the conveying route in synchronization with the robot control processor based on the signal indicating the travel distance received from the encoder device via the input/output interface;
means for initiating the capturing by the image sensor in response to an imaging command; and
means for transmitting, to the robot control processor, the positional information and the travel distance upon the capturing of the image used to acquire the positional information based on the signal indicating the travel distance, wherein the signal indicating the travel distance of the conveyer in the conveying route is a pulse signal, the pulse signal is configured to be input to the image processing apparatus and the robot control processor, the means for maintaining the travel distance includes a first counter that counts the number of pulses included in the pulse signal, an identical parameter is set with respect to counting between the first counter and a second counter, the second counter used by the robot control processor to count the number of pulses included in the pulse signal, and the image sensor and the robot control processor synchronously maintain a same count value as a result thereof.

14. The image processing system according to claim 13, wherein the positional information includes a coordinate value in which the region corresponding to the pre-registered workpiece in the image is expressed in a coordinate system of the robot.

15. The image processing system according to claim 14, wherein the positional information further includes a rotation angle of the region corresponding to the pre-registered workpiece in the image, the rotation angle being based on an attitude of the pre-registered workpiece.

16. The image processing system according to claim 13, wherein the first counter and the second counter are reset before the counting of the number of pulses included in the pulse signal is started.

17. The image processing system according to claim 13, wherein the travel distance upon the capturing of the image used to acquire the positional information is indicated by a counter value of the first counter.

* * * * *